United States Patent [19]
Alizon et al.

[11] Patent Number: 5,976,785
[45] Date of Patent: *Nov. 2, 1999

[54] COMPETITIVE ASSAYS FOR DETERMINING THE EFFECTIVENESS OF A HUMAN IMMUNODEFICIENCY VIRUS TYPE 2 (HIV-2) ANTIVIRAL AGENT, EMPLOYING PEPTIDES AND PROTEINS OF HIV-2

[75] Inventors: Marc Alizon, Paris; Luc Montagnier, Le Plessis Robinson; Denise Guétard, Paris, all of France; Francois Clavel, Rockville, Md.; Pierre Sonigo, Paris; Mireille Guyader, Toulouse, both of France

[73] Assignee: Institut Pasteur, Paris, France

[*] Notice: This patent is subject to a terminal disclaimer.

[21] Appl. No.: 07/811,150

[22] Filed: Dec. 20, 1991

Related U.S. Application Data

[62] Division of application No. 07/752,368, Sep. 3, 1991, which is a division of application No. 07/013,477, Feb. 11, 1987, Pat. No. 5,079,342, which is a continuation-in-part of application No. 07/003,764, Jan. 16, 1987, Pat. No. 5,051,496, which is a continuation-in-part of application No. 06/933,184, Nov. 21, 1986, abandoned, which is a continuation-in-part of application No. 06/916,080, Oct. 6, 1986, and application No. 06/835,228, Mar. 3, 1986, Pat. No. 4,839,288.

[30] Foreign Application Priority Data

| Jan. 22, 1986 | [FR] | France | 86 00911 |
| Feb. 6, 1986 | [FR] | France | 86 01635 |
| Feb. 13, 1986 | [FR] | France | 86 01985 |
| Mar. 18, 1986 | [FR] | France | 86 03881 |
| Mar. 24, 1986 | [FR] | France | 86 04215 |

[51] Int. Cl.$^6$ ............................................. C12Q 1/70
[52] U.S. Cl. .............................. 435/5; 435/7.1; 435/7.2; 435/7.8; 435/7.9; 530/324; 530/350
[58] Field of Search ................................. 435/5, 7.1, 7.2, 435/7.8, 7.9; 530/350, 324

[56] References Cited

U.S. PATENT DOCUMENTS

| 4,629,783 | 12/1986 | Cosand . |
| 4,839,288 | 6/1989 | Montagnier et al. . |
| 5,079,342 | 1/1992 | Alizon et al. . |

FOREIGN PATENT DOCUMENTS

| 0 316 695 B1 | 3/1993 | European Pat. Off. . |

| WO 85/04897 | 11/1985 | WIPO . |

OTHER PUBLICATIONS

Clavel et al., "Isolation of a New Human Retrovirus from West African Patients with AIDS", Science, 233, pp. 343–346 (1986).
Allan et al., "Major Glycoprotein Antigens That Induce Antibodies in AIDS Patients Are Encoded by HTLV–III", Science 228, pp. 1091–1094 (1985).
Chang et al., "Detection of Antibodies to Human T–Cell Lymphotropic Virus–III (HTLV–III)with an Immunoassay Employing a Recombinant *Escherichia coli*–Derived Viral Antigenic Peptide", Bio/Technology, 3, pp. 905–909 (1985).
Kanki et al., "Isolation of T–lymphotropic Retrovirus Related to HTLV–III/LAV from Wild–Caught African Green Monkeys" Science, 230, pp. 951–954 (1985).
Kanki et al., "Serologic Identification and Characterization of a Macaque T–lymphotropic Retrovirus Closely Related to HTLV–III", Science, 228, pp. 1199–1201 (1985).
Clavel et al., "LAV type II: un second retrovirus associe au SIDA en Afrique de l'Ouest", Compte Rendus De L'Academie Des Sciences Paris, Serie III, 302, pp. 485–488 (1986).
Klatzmann et al., "T–lymphocyte T4 Molecule Behaves As The Receptor For Human Retrovirus LAV", Nature, 312, pp. 767–768 (1984).
Daniel et al., "Isolation of T–Cell Tropic HTLV–III–like Retrovirus from Macaques", Science, 228, pp. 1201–1204 (1985).
Barin et al., "Serological Evidence For Virus Related To Simian T–lymphotropic Retrovirus III in Residents of West Africa", The Lancet, No. 8469/70, pp. 1387–1389 (Dec. 21/28, 1985).
Mitsuza et al, Retroviruses in Human Lymphoma Leukemia Miwa et al, (eds) Japan Sci Press Tokyo 1985 pp. 277–288.
Sandström et al Drugs 34:372–90 1987.
Klatzmann et al: T–Lymphocyte T4 . . . retrovirus LAV Nature V312 Dec. 20, 1984.

*Primary Examiner*—Jeffrey Stucker
*Attorney, Agent, or Firm*—Finnegan, Henderson, Farabow, Garrett & Dunner

[57] ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

12 Claims, 5 Drawing Sheets

COMPETITIVE ASSAYS FOR DETERMINING THE EFFECTIVENESS OF A HUMAN IMMUNODEFICIENCY VIRUS TYPE 2 (HIV-2) ANTIVIRAL AGENT, EMPLOYING PEPTIDES AND PROTEINS OF HIV-2

BACKGROUND OF THE INVENTION

This application is a division of application Ser. No. 07/752,368, filed Sep. 3, 1991, which is a division of application Ser. No. 013,477, filed Feb. 11, 1987, now U.S. Pat. No. 5,079,342, issued Jan. 7, 1992, which is continuation-in-part of allowed U.S. patent application Ser. No. 07/003,764 of Alizon et al. for "Cloned DNA Sequences Related to the Entire Genomic RNA of Human Immunodeficiency Virus II (HIV-2), Polypeptides Encoded by these DNA Sequences and Use of these DNA Clones and Polypeptides in Diagnostic Kits," filed Jan. 16, 1987, now U.S. Pat. No. 5,051,496, which is a continuation-in-part of U.S. patent application Ser. No. 06/933,184 filed Nov. 21, 1986, now abandoned in favor of continuation application Ser. No. 604,323, filed Oct. 24, 1990, now abandoned in favor of continuation application Ser. No. 732,748, filed Jul. 18, 1991 (pending) which is a continuation-in-part application of U.S. patent application Ser. No. 916,080 of Montagnier et al. for "Cloned DNA Sequences Related to the Genomic RNA of the Human Immunodeficiency Virus II (HIV-2), Polypeptides Encoded by these DNA Sequences and Use of these DNA Clones and Polypeptides in Diagnostic Kits," filed Oct. 6, 1986, now abandoned in favor of continuation application Ser. No. 602,383, filed Oct. 24, 1990 (now abandoned), and U.S. patent application Ser. No. 835,228 of Montagnier et al. for "New Retrovirus Capable of Causing AIDS, Antigens Obtained from this Retrovirus and Corresponding Antibodies and their Application for Diagnostic Purposes," filed Mar. 3, 1986 (now U.S. Pat. No. 4,839,288, issued Jun. 13, 1989). The disclosures of each of these predecessor applications are expressly -incorporated herein by reference.

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECACC under No. 87.001.001 on Jan. 9, 1987. A second LAV-II isolate was deposited at CNCM on Feb. 21, 1986 under Accession No. I-532 and has also been deposited at the British ECACC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

In accordance with a further object of the present invention, a peptide is provided as described above, either along or conjugated to a carrier molecule, the peptide being capable of eliciting the production of an antibody to the peptide, and said antibody is capable of forming an effective immunocomplex with the entire HIV-2 retrovirus or with its corresponding proteins.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2. In FIG. 1B, the symbols B, H, Ps and Pv refer to the restriction sites BamHI, HindIII, PstI and PvuII, respectively.

FIG. 3 generally depicts a restriction map of the HIV-2 ROD genome and its homology to HIV-1. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

DETAILED DESCRIPTION OF THE PREFERRED EMBODIMENTS

Reference will now be made in detail to the presently preferred embodiments of the invention, which, together with the following examples, serve to explain the principles of the invention.

Figures 1A, 1B:
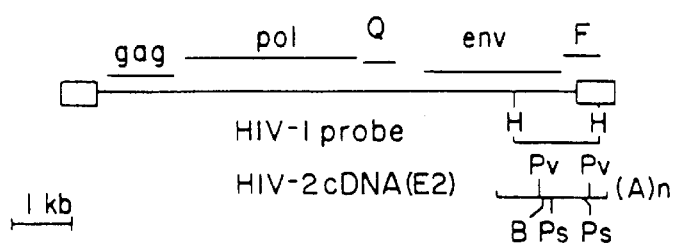
FIG. 1A depicts the genetic organization of HIV-1, position of the HIV-1 HindII fragment used as a probe to screen the cDNA library, and restriction map of the HIV-2 cDNA clone, E2.
FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed.
Figure 2A:
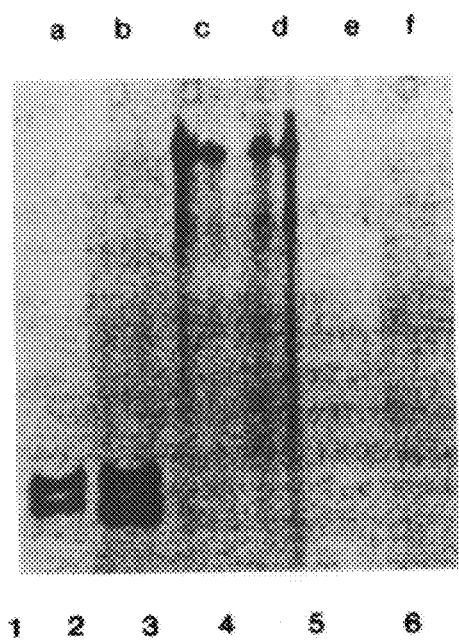
FIGS. 2A and B are lines drawing representing Southern blots of DNA extracted from CEM cells infected with the following isolates: HIV-$2_{ROD}$ (a,c), HIV-$2_{DUL}$ (b,d), and HIV-$1_{BRU}$ (e.f). DNA in lanes a,b,f was Pst I digested; in c,d,e DNA was undigested.
Figure 2B:
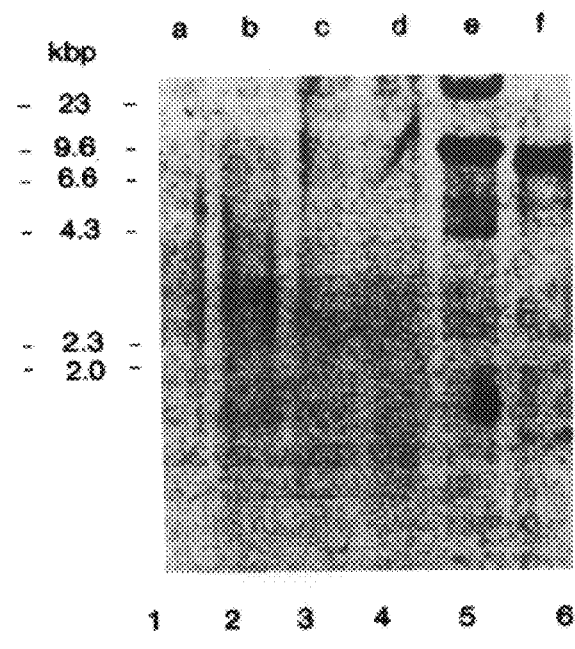
FIG. 2 generally depicts the HIV-2 specificity of the E2 clone.
FIGS. 2C and D are line drawing representing dot blot hybridization of pelleted virions from CEM cells infected by the HIV-$1_{BRU}$(1), Simian Immunodeficiency Virus (SIV) isolate Mm 142-83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIGS. 2A and C depict hybridization with the HIV-2 cDNA (E2) and FIGS. 2B and D depict hybridization to an HIV-1 probe consisting of a 9 Kb SacI insert from HIV-1 BRU(clone lambda J 19).
Figure 2C:
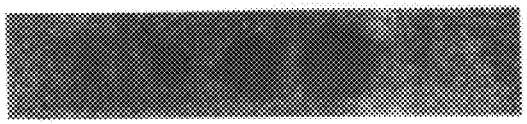
Figure 2D:
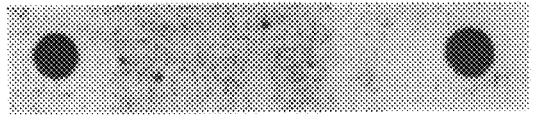

The genetic structure of the HIV-2 virus has been analyzed by molecular cloning according to the method set forth herein and in the Examples. A restriction map of the genome of this virus is included in FIG. 5. In addition, the partial sequence of a CDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) probed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the LAVBRU isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundred insertions/deletions need to be introduced in comparison, the homology of the corresponding domains in HIV-1 isolates from USA and Africa is greater than 95% and no insertions or deletions are seen.

Figure 4A:
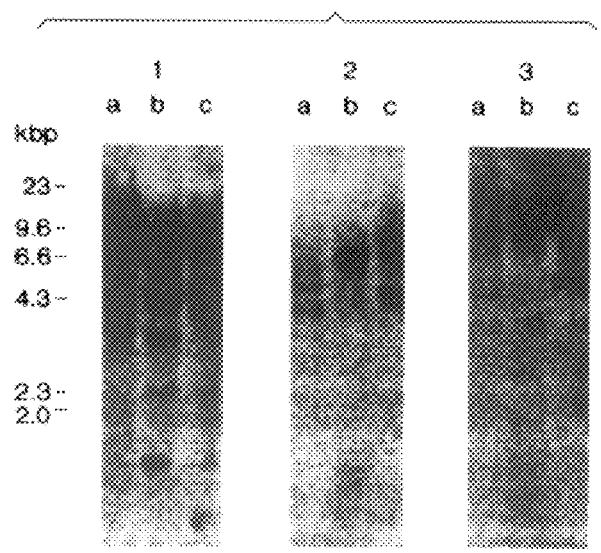
FIG. 4A is a line drawing depicting DNA (20 μg. per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/μg.
Figure 4B:
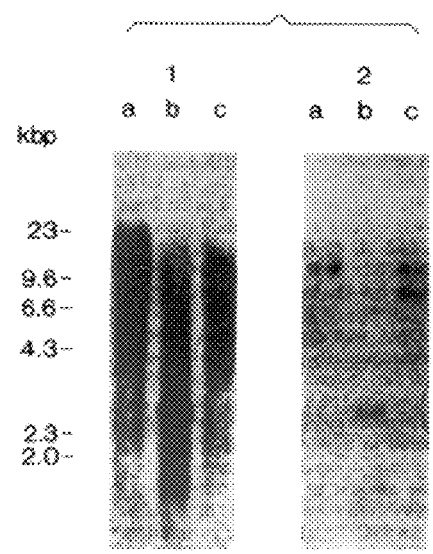
FIG. 4B is a line drawing depicting DNA from HUT 78 (a human T lymphoid cell line) cells infected with STLV3 MAC isolate Mm 142–83. The same amounts of DNA and enzymes were used as indicated in panel A. Hybridization was performed with the same probe as in A, but in non-stringent conditions. As described in Example 1 washing was for one hour in 2× SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIGS. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-2$_{ROD}$.

About $2 \times 10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
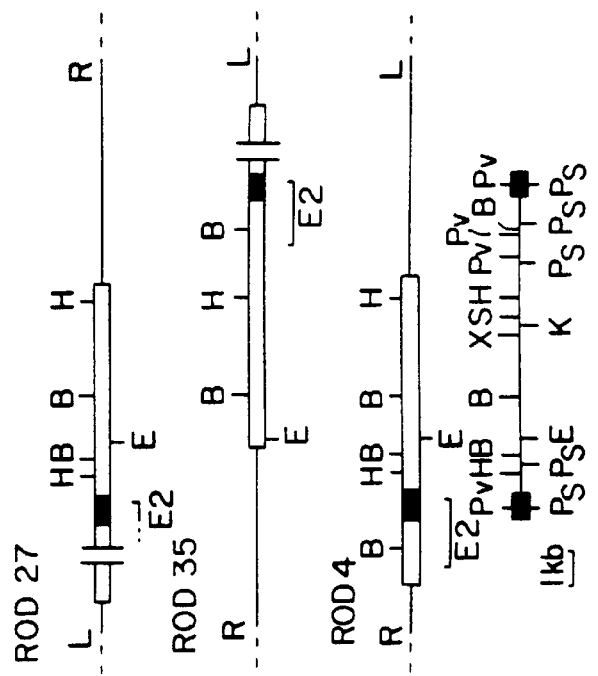
FIG. 3A specifically depicts the organization of three recombinant phage lambda clones, ROD 4, ROD 27, and ROD 35.
Figure 3B:
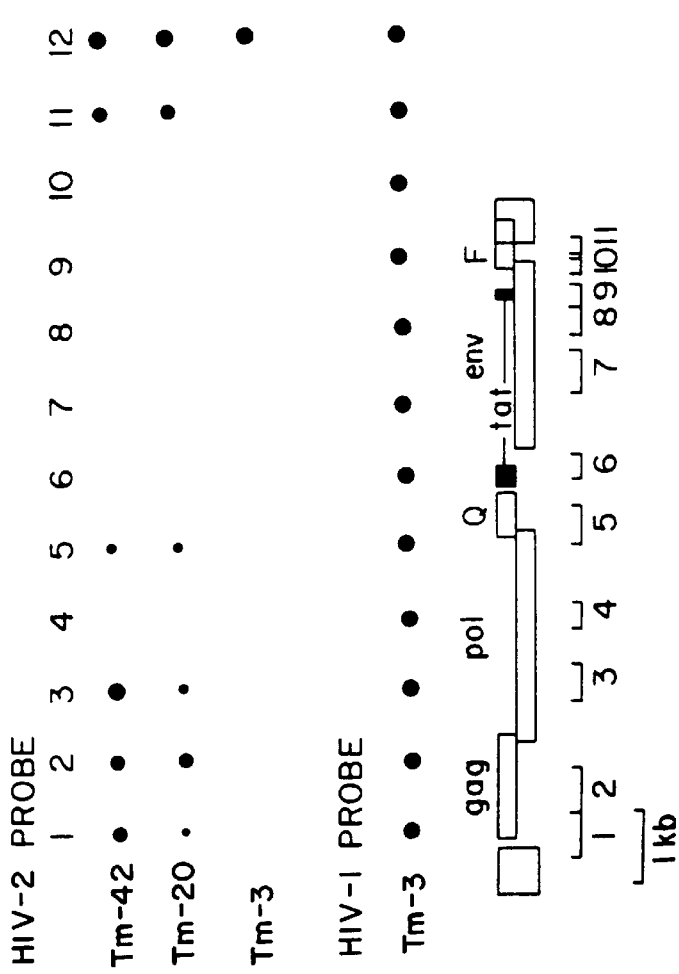
FIG. 3B specifically depicts dots 1–11 which correspond to the single-stranded DNA form of M13 subclones from the HIV-$1_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2× SSC, 0.1% SDS at 25° C. (Tm −42° C.), 4× SSC, 0.1% SDS at 60° C. (Tm −20° C.), and 0.1× SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-$1_{BRU}$ genome. HIV-1 and HIV-2 probes were labelled the same specific activity ($10^8$ cpm/g.).

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2 Kb of the HIV-2 genome and cellular flanking sequences (5' LTR and 5' viral coding sequences to the EcoRI site). Plasmid p ROD 4-8 is derived from λROD 4 and contains the about 5 Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 Kb of cellular flanking sequences.

Figure 5:
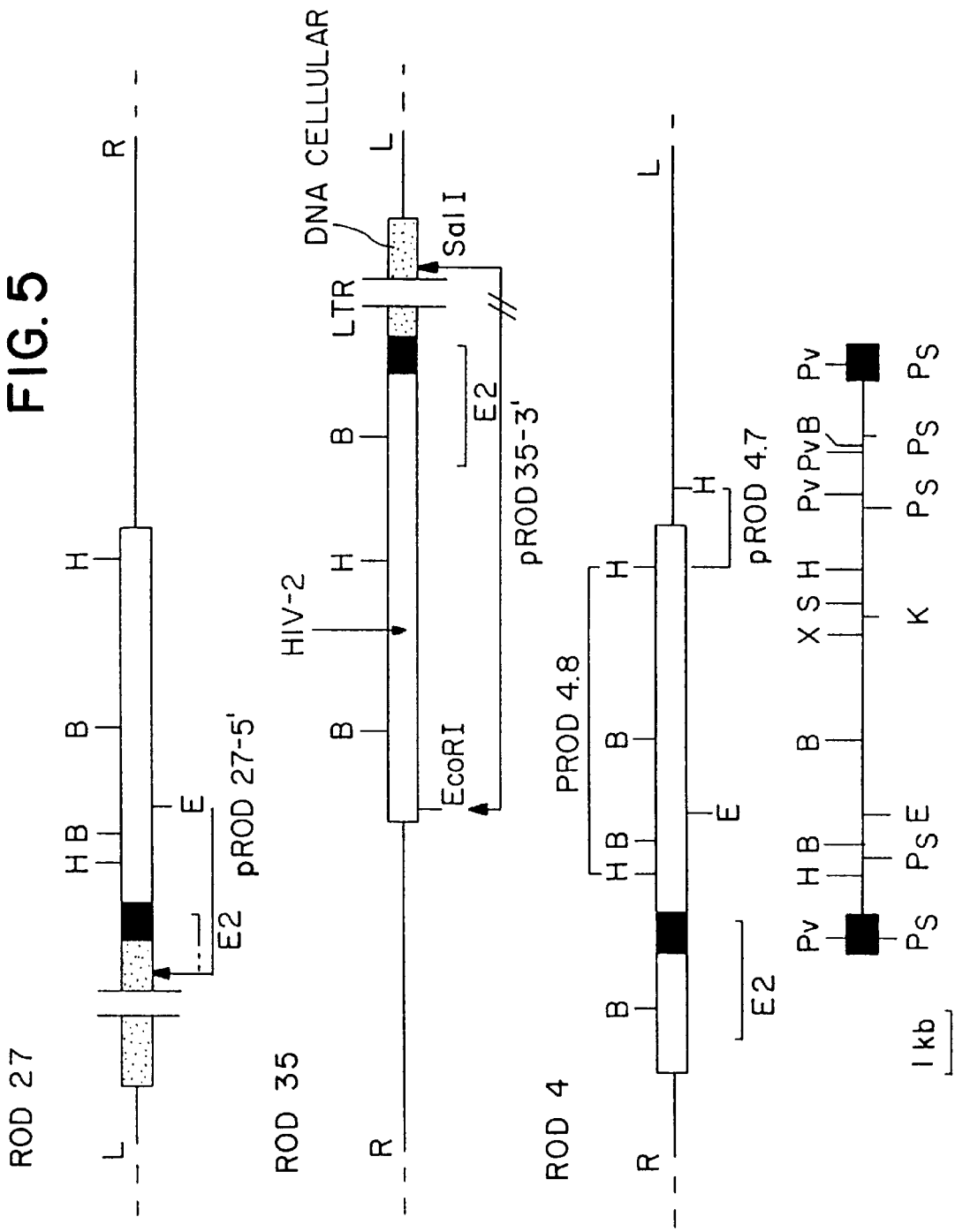
FIG. 5 depicts the position of derived plasmids from λROD 27, λROD 35 and λROD 4.

Plasmid pROD 27-5' and pROD 35 in *E. coli* strain HB 101 are deposited respectively under No. I-626 and I-633 at the CNCM, and have also been deposited at the NCIB (British Collection). These plasmids are depicted in FIG. 5. Plasmids pROD 4–7 and pROD 4–8 in *E. coli* strain TG1 are deposited respectively under No. I-627 and I-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm−42° C.), the hybridization of HIV-1 and 2 was restricted to a fraction of their genomes, principally the qaq gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., *Cell* 40:63–74 (1986).

It was observed that HIV-2 is related more closely to the Simian Immunodeficiency Virus (SIV) than it is to HIV-1. This correlation has been described by F. Clavel et al. in C. R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-$2_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-$2_{ROD}$. it is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., *Nature* 324 (18):691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cONA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1: Cloning of a cDNA Complementary to Genomic RNA From HIV-2 Virions HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TGl strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}P$ labelled to a specific activity of $10^9$ cpm μg. The filters were prehybridized in 5×SSC, 5× Denhardt solution, 25% formamide, and denatured salmon sperm DNA (100 μg/ml.) at 37° C. for 4 hours and hybridized for 16 hours in the same buffer (Tm −42° C.) plus $4\times10^7$ cpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2: Hybridization of DNA from HIV-1 and HIV-2 Infected Cells and RNA from HIV-1 and 2 and SIV Virons With a Probe Derived From an HIV-2 Cloned CDNA DNA was extracted from infected CEM cells continuously producing HIV-1 or 2. The DNA digested with 20 μg of PstI or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5×Denhard solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/μg.) for 16 hours at 42° C. Washing was in 0.1×SSC, 0.1% SDS for 2×30 mn. After exposition for 16 hours with intensifying screens, the Southern blot was dehybridized in 0.4 N NaOH, neutralized, and rehybridized in the same conditions to the HIV-1 probe labelled to $10^9$ cpm/μg.

Example 3: Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2\times10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4: Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546-2111) expresses a protein product having a molecular weight of around 55 kd and is cleaved into the following proteins:
   a) p 16 (546-950)
   b) p 26 (951-1640)
   c) p 12 (1701-2111)
2) polymerase (1829-4936)
3) Q protein (4869-5513)
4) R protein (5682-5996)
5) X protein (5344-5679)
6) Y protein (5682-5996)
7) Env protein (6147-8720)
8) F protein (8557-9324)
9) TAT gene (5845-6140 and 8307-8400) is expressed by two exons separated by introns.
10) ART protein (6071-6140 and 8307-8536) is similarly the expression product of two exons.
11) LTR:R (1-173 and 9498-9671)
12) U5 (174-299)
13) U3 (8942-9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG

.         .         .         .         .         .
GTAGAGCCTGGGTGTTCCCTGCTAGACTCTCACCAGCACTTGGCCGGTGCTGGGCAGACG

.         .         .       100         .         .
GCCCCACGCTTGCTTGCTTAAAAACCTCTTAATAAAGCTGCCAGTTAGAAGCAAGTTAAG

.         .         .         .         .         .
TGTGTGCTCCCATCTCTCCTAGTCGCCGCCTGGTCATTCGGTGTTCACCTGAGTAACAAG

.       200         .         .         .         .
ACCCTGGTCTGTTAGGACCCTTCTTGCTTTGGGAAACCGAGGCAGGAAAATCCCTAGCAG

.         .         .         .       300         .
GTTGGCGCCTGAACAGGGACTTGAAGAAGACTGAGAAGTCTTGGAACACGGCTGACTGAA

.         .         .         .         .         .
GGCAGTAAGGGCGGCAGGAACAAACCACGACGGAGTGCTCCTAGAAAGGCGCGGGCCGAG

.         .       400         .         .         .
GTACCAAAGGCAGCGTGTGGAGCGGGAGGAGAAGAGGCCTCCGGGTGAAGGTAAGTACCT

.         .         .         .         .         .
ACACCAAAAACTGTAGCCGAAAGGGCTTGCTATCCTACCTTTAGACAGGTAGAAGATTGT
                        500         .         .         .         .
             MetGlyAlaArgAsnSerValLeuArgGlyLysLysAlaAspGluLeuGluArgIle
GGGAGATGGGCGCGAGAAACTCCGTCTTGAGGGGAAAAAAGCAGATGAATTAGAAAGAA

.         .         .         .         .       600
   ArgLeuArgProGlyGlyLysLysLysTyrArgLeuLysHisIleValTrpAlaAlaAsn
TCAGGTTACGGCCCGGCGGAAAGAAAAAGTACAGGCTAAAACATATTGTGTGGGCAGCGA

.         .         .         .         .         .
   LysLeuAspArgPheGlyLeuAlaGluSerLeuLeuGluSerLysGluGlyCysGlnLys
ATAAATTGGACAGATTCGGATTACCAGAGAGCCTGTTGGAGTCAAAAGAGGGTTGTCAAA

.         .         .       700         .         .
   IleLeuThrValLeuAspProMetValProThrGlySerGluAsnLeuLysSerLeuPhe
AAATTCTTACAGTTTTAGATCCAATGGTACCGACAGGTTCAGAAAATTTAAAAAGTCTTT

.         .         .         .         .         .
   AsnThrValCysValIleTrpCysIleHisAlaGluGluLysValLysAspThrGluGly
TTAATACTGTCTGCGTCATTTGGTGCATACACGCAGAAGAGAAAGTGAAAGATACTGAAG

.       800         .         .         .         .
   AlaLysGlnIleValArgArgHisLeuValAlaGluThrGlyThrAlaGluLysMetPro
GAGCAAAACAAATAGTGCGGAGACATCTAGTGGCAGAAACAGGAACTGCAGAGAAAATGC

.         .         .         .         .       900
   SerThrSerArgProThrAlaProSerSerGluLysGlyGlyAsnTyrProValGlnHis
CAAGCACAAGTAGACCAACAGCACCATCTAGCGAGAAGGGAGGAAATTACCCAGTGCAAC

.         .         .         .         .         .
   ValGlyGlyAsnTyrThrHisIleProLeuSerProArgThrLeuAsnAlaTrpValLys
ATGTAGGCGGCAACTACACCCATATACCGCTGAGTCCCCGAACCCTAAATGCCTGGGTAA

.         .         .      1000         .         .
   LeuValGluGluLysLysPheGlyAlaGluValValProGlyPheGlnAlaLeuSerGlu
AATTAGTAGAGGAAAAAAAGTTCGGGGCAGAAGTAGTGCCAGGATTTCAGGCACTCTCAG

.         .         .         .         .         .
   GlyCysThrProTyrAspIleAsnGlnMetLeuAsnCysValGlyAspHisGlnAlaAla
AAGGCTGCACGCCCTATGATATCAACCAAATGCTTAATTGTGTGGGCGACCATCAAGCAG

.      1100         .         .         .         .
   MetGlnIleIleArgGluIleIleAsnGluGluAlaAlaGluTrpAspValGlnLisPro
CCATGCAGATAATCAGGGAGATTATCAATGAGGAAGCAGCAGAATGGGATGTGCAACATC

.         .         .         .       1200         .
   IleProGlyProLeuProAlaGlyGlnLeuArgGluProArgGlySerAspIleAlaGly
CAATACCAGGCCCCTTACCAGCGGGGCAGCTTAGAGAGCCAAGGGGATCTGACATAGCAG

.         .         .         .         .         .
   ThrThrSerThrValGluGluGlnIleGlnTrpMetPheArgProGlnAsnProValPro
CGACAACAAGCACAGTAGAAGAACAGATCCAGTGGATGTTTAGGCCACAAAATCCTGTAC

.         .         .      1300         .         .
   ValGlyAsnIleTyrArgArgTrpIleGlnIleGlyLeuGlnLysCysValArgMetTyr
CAGTAGGAAACATCTATAGAAGATGGATCCAGATAGGATTGCAGAAGTGTGTCAGGATGT
```

```
                AsnProThrAsnIleLeuAspIleLysGlnGlyProLysGluProPheGlnSerTyrVal
           ACAACCCGACCAACATCCTAGACATAAAACAGGGACCAAAGGAGCCGTTCCAAAGCTATG

1400              .         .         .         .
                AspArgPheTyrLysSerLeuArgAlaGluGlnThrAspProAlaValLysAsnTrpMet
           TAGATAGATTCTACAAAAGCTTGAGGGCAGAACAAACAGATCCAGCAGTGAAGAATTGGA

.         .         .         .         .        1500
                ThrGlnThrLeuLeuValGlnAsnAlaAsnProAspCysLysLeuValLeuLysGlyLeu
           TGACCCAAACACTGCTAGTACAAAATGCCAACCCAGACTGTAAATTAGTGCTAAAAGGAC

.         .         .         .         .         .
                GlyMetAsnProThrLeuGluGluMetLeuThrAlaCysGlnGlyValGlyGlyProGly
           TAGGGATGAACCCTACCTTAGAAGAGATGCTGACCGCCTGTCAGGGGGTAGGTGGGCCAG

.         .         .        1600        .         .
                GlnLysAlaArgLeuMetAlaGluAlaLeuLysGluValIleGlyProAlaProIlePro
           GCCAGAAAGCTAGATTAATGGCAGAGGCCCTGAAAGAGGTCATAGGACCTGCCCCTATCC

.         .         .         .         .         .
                PheAlaAlaAlaGlnGlnArgLysAlaPheLysCysTrpAsnCysGlyLysGluGlyHis
           CATTCGCAGCAGCCCAGCAGAGAAAGGCATTTAAATGCTGGAACTGTGGAAAGGAAGGGC

1700              .         .         .         .
                SerAlaArgGlnCysArgAlaProArgArgGlnGlyCysTrpLysCysGlyLysProGly
           ACTCGGCAAGACAATGCCGAGCACCTAGAAGGCAGGGCTGCTGGAAGTGTGGTAAGCCAG

.         .         .         .        1800        .
                                           ThrGlyArgPhePheArgThrGlyProLeuGly
                HisIleMetThrAsnCysProAspArgGlnAlaGlyPheLeuGlyLeuGlyProTrpGly
           GACACATCATGAGAAACTGCCCAGATAGACAGGCAGGTTTTTTAGGACTGGGCCCTTGGG

.         .         .         .         .         .
                LysGluAlaProGlnLeuProArgGlyProSerSerAlaGlyAlaAspThrAsnSerThr
                LysLysProArgAsnPheProValAlaGlnValProGlnGlyLeuThrProThrAlaPro
           GAAAGAAGCCGCGCAACTTCCCCGTGGCCCAAGTTCCGCAGGGGCTGACACCAACAGCAC

.         .         .        1900        .         .
                ProSerGlySerSerSerGlySerThrGlyGluIleTyrAlaAlaArgGluLysThrGlu
                ProValAspProAlaValAspLeuLeuGluLysTyrMetGlnGlnGlyLysArgGlnArg
           CCCCAGTGGATCCAGCAGTGGATCTACTGGAGAAATATATGCAGCAAGGGAAAAGACAGA

.         .         .         .         .         .
                ArgAlaGluArgGluThrIleGlnGlySerAspArgGlyLeuThrAlaProArgAlaGly
                GluGlnArgGluArgProTyrLysGluValThrGluAspLeuLeuHisLeuGluGlnGly
           GAGAGCAGAGAGAGAGACCATACAAGGAAGTGACAGAGGACTTACTGCACCTCGAGCAGG

2000              .         .         .         .
                GlyAspThrIleGlnGlyAlaThrAsnArgGlyLeuAlaAlaProGlnPheSerLeuTrp
                GluThrProTyrArgGluProProThrGluAspLeuLeuHisLeuAsnSerLeuPheGly
           GGGAGACACCATACAGGGAGCCACCAACAGAGGACTTGCTGCACCTCAATTCTCTCTTTG

.         .         .         .         .        2100
                LysArgProValValThrAlaTyrIleGluGlyGlnProValGluValLeuLeuAspThr
                LysAspGln
           GAAAAGACCAGTAGTCACAGCATACATTGAGGGTCAGCCAGTAGAAGTCTTGTTAGACAC

.         .         .         .         .         .
                GlyAlaAspAspSerIleValAlaGlyIleGluLeuGlyAsnAsnTyrSerProLysIle
           AGGGGCTGACGACTCAATAGTAGCAGGAATAGAGTTAGGGAACAATTATAGCCCAAAAAT

.         .        2200        .         .         .
                ValGlyGlyIleGlyGlyPheIleAsnThrLysGluTyrLysAsnValGluIleGluVal
           AGTAGGGGGAATAGGGGGATTCATAAATACCAAGGAATATAAAAATGTAGAAATAGAAGT

.         .         .         .         .         .
                LeuAsnLysLysValArgAlaThrIleMetThrGlyAspThrProIleAsnIlePheGly
           TCTAAATAAAAAGGTACGGGCCACCATAATGACAGGCGACACCCCAATCAACATTTTTGG

2300              .         .         .         .
                ArgAsnIleLeuThrAlaLeuGlyMetSerLeuAsnLeuProValAlaLysValGluPro
           CAGAAATATTCTGACAGCCTTAGGCATGTCATTAAATCTACCAGTCGCCAAAGTAGAGCC

.         .         .         .         .        2400
                IleLysIleMetLeuLysProGlyLysAspGlyProLysLeuArgGlnTrpProLeuThr
           AATAAAAATAATGCTAAAGCCAGGGAAAGATGGACCAAAACTGAGACAATGGCCCTTAAC

.         .         .         .         .         .
                LysGluLysIleGluAlaLeuLysGluIleCysGluLysMetGluLysGluGlyGlnLeu
```

```
AAAAGAAAAAATAGAAGCACTAAAAGAAATCTGTGAAAAAATGGAAAAAGAAGGCCAGCT
                                    2500        .         .
  GluGluAlaProProThrAsnProTyrAsnThrProThrPheAlaIleLysLysLysAsp
AGAGGAAGCACCTCCAACTAATCCTTATAATACCCCCACATTTGCAATCAAGAAAAAGGA

LysAsnLysTrpArgMetLeuIleAspPheArgGluLeuAsnLysValThrGlnAspPhe
CAAAAACAAATGGAGGATGCTAATAGATTTCAGAGAACTAAACAAGGTAACTCAAGATTT
                      2600        .         .         .
  ThrGluIleGlnLeuGlyIleProHisProAlaGlyLeuAlaLysLysArgArgIleThr
CACAGAAAATTCAGTTAGGAATTCCACACCCAGCAGGGTTGGCCAAGAAGAGAAGAATTAC
                                              2700        .
  ValLeuAspValGlyAspAlaTyrPheSerIleProLeuHisGluAspPheArgProTyr
TGTACTAGATGTAGGGGATGCTTACTTTTCCATACCACTACATGAGGACTTTAGACCATA

ThrAlaPheThrLeuProSerValAsnAsnAlaGluProGlyLysArgTyrIleTyrLys
TACTGCATTTACTCTACCATCAGTGAACAATGCAGAACCAGGAAAAAGATACATATATAA
                                    2800        .         .
  ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT

LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
                      2900        .         .         .
  LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
                                              3000        .
  LeuLeuAsnGlyLeuGlyPheSerThrProAspGluLysPheGlnLysAspProProTyr
ACTTCTAAATGGCCTAGGATTTTCTACCCCAGATGAGAAGTTCCAAAAAGACCCTCCATA

HisTrpMetGlyTyrGluLeuTrpProThrLysTrpLysLeuGlnLysIleGlnLeuPro
CCACTGGATGGGCTATGAACTATGGCCAACTAAATGGAAGTTGCAGAAAATACAGTTGCC
                                    3100        .         .
  GlnLysGluIleTrpThrValAsnAspIleGlnLysLeuValGlyValLeuAsnTrpAla
CCAAAAAGAAATATGGACAGTCAATGACATCCAGAAGCTAGTGGGTGTCCTAAATTGGGC

AlaGlnLeuTyrProGlyIleLysThrLysHisLeuCysArgLeuIleArgGlyLysMet
AGCACAACTCTACCCAGGGATAAAGACCAAACACTTATGTAGGTTAATCAGAGGAAAAAT
                      3200        .         .         .
  ThrLeuThrGluGluValGlnTrpThrGluLeuAlaGluAlaGluLeuGluGluAsnArg
GACACTCACAGAAGAAGTACAGTGGACAGAATTACCAGAAGCAGAGCTAGAAGAAAACAG
                                              3300        .
  IleIleLeuSerGlnGluGlnGluGlyHisTyrTyrGlnGluGluLysGluLeuGluAla
AATTATCCTAAGCCAGGAACAAGAGGGACACTATTACCAAGAAGAAAAAGAGCTAGAAGC

ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
                                    3400        .         .
  LeuLysValGlyLysTyrAlaLysValLysAsnThrHisThrAsnGlyIleArgLeuLeu
TCTAAAAGTAGGAAAATATGCAAAGGTGAAAAACACCCATACCAATGGAATCAGATTGTT

AlaGlnValValGlnLysIleGlyLysGluAlaLeuValIleTrpGlyArgIleProLys
AGCACAGGTAGTTCAGAAAATAGGAAAAGAAGCACTAGTCATTTGGGGACCAATACCAAA
                      3500        .         .         .
  PheHisLeuProValGluArgGluIleTrpGluGlnTrpTrpAspAsnTyrTrpGlnVal
ATTTCACCTACCAGTAGAGAGAGAAATCTGGGAGCAGTGGTGGGATAACTACTGGCAAGT
                                              3600        .
  ThrTrpIleProAspTrpAspPheValSerThrProProLeuValArgLeuAlaPheAsn
GACATGGATCCCAGACTGGGACTTCGTGTCTACCCCACCACTGGTCAGGTTAGCGTTTAA

LeuValGlyAspProIleProGlyAlaGluThrPheTyrThrAspGlySerCysAsnArg
CCTGGTAGGGGATCCTATACCAGGTGCAGAGACCTTCTACACAGATCGATCCTGCAATAG
```

```
                                 3700      .        .
  GlnSerLysGluGlyLysAlaGlyTyrValThrAspArgGlyLysAspLysValLysLys
  GCAATCAAAAGAAGGAAAAGCAGGATATGTAACAGATAGAGGGAAAGACAAGGTAAAGAA

LeuGluGlnThrThrAsnGlnGlnAlaGluLeuGluAlaPheAlaMetAlaLeuThrAsp
  ACTAGAGCAAACTACCAATCAGCAAGCAGAACTAGAAGCCTTTGCGATGGCACTAACAGA

.      3800          .        .
  SerGlyProLysValAsnIleIleValAspSerGlnTyrValMetGlyIleSerAlaSer
  CTCGGGTCCAAAAGTTAATATTATAGTAGACTCACAGTATGTAATGGGGATCAGTGCAAG

.        .        .        .      3900
  GlnProThrGluSerGluSerLysIleValAsnGlnIleIleGluGluMetIleLysLys
  CCAACCAACAGAGTCAGAAAGTAAAATAGTGAACCAGATCATAGAAGAAATGATAAAAAA

GluAlaIleTyrValAlaTrpValProAlaHisLysGlyIleGlyGlyAsnGlnGluVal
  GGAAGCAATCTATGTTGCATGGGTCCCAGCCCACAAAGGCATAGGGGGAAACCAGGAAGT

.        .        .      4000          .
  AspHisLeuValSerGlnGlyIleArgGlnValLeuPheLeuGluLysIleGluProAla
  AGATCATTTAGTGAGTCAGGGTATCAGACAAGTGTTGTTCCTGGAAAAAATAGAGCCCGC

GlnGluGluHisGluLysTyrHisSerAsnValLysGluLeuSerHisLysPheGlyIle
  TCAGGAAGAACATGAAAAATATCATAGCAATGTAAAAGAACTGTCTCATAAATTTGGAAT

.      4100          .        .
  ProAsnLeuValAlaArgGlnIleValAsnSerCysAlaGlnCysGlnGlnLysGlyGlu
  ACCCAATTTAGTGGCAAGGCAAATAGTAAACTCATGTGCCCAATGTCAACAGAAAGGGGA

.        .        .        .      4200
  AlaIleHisGlyGlnValAsnAlaGluLeuGlyThrTrpGlnMetAspCysThrHisLeu
  AGCTATACATGGGCAAGTAAATGCAGAACTAGCCACTTGGCAAATGGACTGCACACATTT

GluGlyLysIleIleIleValAlaValHisValAlaSerGlyPheIleGluAlaGluVal
  AGAAGGAAAGATCATTATAGTAGCAGTACATGTTGCAAGTGGATTTATAGAAGCAGAAGT

.        .        .      4300          .
  IleProGlnGluSerGlyArgGlnThrAlaLeuPheLeuLeuLysLeuAlaSerArgTrp
  CATCGCACAGGAATCAGGAAGACAAACAGCACTCTTCCTATTGAAACTGGCAAGTAGGTG

ProIleThrHisLeuHisThrAspAsnGlyAlaAsnPheThrSerGlnGluValLysMet
  GCCAATAACACACTTGCATACAGATAATGGTGCCAACTTCACTTCACAGGAGGTGAAGAT

.      4400          .        .
  ValAlaTrpTrpIleGlyIleGluGlnSerPheGlyValProTyrAsnProGlnSerGln
  GGTAGCATGGTGGATAGGTATAGAACAATCCTTTGGAGTACCTTACAATCCACAGAGCCA

.        .        .        .      4500
  GlyValValGluAlaMetAsnHisHisLeuLysAsnGluIleSerArgIleArgGluGln
  AGGAGTAGTAGAAGCAATGAATCACCATCTAAAAAACCAAATAAGTAGAATCAGAGAACA

AlaAsnThrIleGluThrIleValLeuMetAlaIleHisCysMetAsnPheLysArgArg
  GGCAAATACAATAGAAACAATAGTACTAATGGCAATTCATTGCATGAATTTTAAAAGAAG

.        .        .      4600          .
  GlyGlyIleGlyAspMetThrProSerGluArgLeuIleAsnMetIleThrThrGluGln
  GGGGGGAATAGGGGATATGACTCCATCAGAAAGATTAATCAATATGATCACCACAGAACA

GluIleGlnPheLeuGlnAlaLysAsnSerLysLeuLysAspPheArgValTyrPheArg
  AGAGATACAATTCCTCCAAGCCAAAAATTCAAAATTAAAAGATTTTCGGGTCTATTTCAG

.      4700          .        .
  GluGlyArgAspGlnLeuTrpLysGlyProGlyGluLeuLeuTrpLysGlyGluGlyAla
  AGAAGGCAGACATCAGTTGTGGAAAGGACCTGGGGAACTACTGTGGAAAGGAGAAGGAGC

.        .        .        .      4800
  ValLeuValLysValGlyThrAspIleLysIleIleProArgArgLysAlaLysIleIle
  AGTCCTAGTCAAGGTAGGAACAGACATAAAAATAATACCAAGAAGGAAAGCCAAGATCAT

ArgAspTyrGlyGlyArgGlnGluMetAspSerGlySerHisLeuGluGlyAlaArgGlu
           MetGluGluAspLysArgTrpIleValValProThrTrpArgValProGlyArg
  CAGACACTATGGAGGAAGACAAGAGATGGATAGTGGTTCCCACCTGGAGGGTGCCAGGGA
```

-continued

```
                          4900
AspGlyGluMetAla
  MetGluLysTrpHisSerLeuValLysTyrLeuLysTyrLysThrLysAspLeuGluLys
  GGATGGAGAAATGGCATAGCCTTGTCAAGTATCTAAAATACAAAACAAAGGATCTAGAAA

ValCysTyrValProHisHisLysValGlyTrpAlaTrpTrpThrCysSerArgValIle
  AGGTGTGCTATGTTCCCCACCATAAGGTGGGATGGGCATGGTGGACTTGCAGCAGGGTAA

5000
    PheProLeuLysGlyAsnSerHisLeuGluIleGlnAlaTyrTrpAsnLeuThrProGlu
  TATTCCCATTAAAAGGAAACAGTCATCTAGAGATACAGGCATATTGGAACTTAACACCAG

5100
      LysGlyTrpLeuSerSerTyrSerValArgIleThrTrpTyrThrGluLysPheTrpThr
  AAAAAGGATGGCTCTCCTCTTATTCAGTAAGAATAACTTGGTACACAGAAAAGTTCTGGA

AspValThrProAspCysAlaAspValLeuIleHisSerThrTyrPheProCysPheThr
  CAGATGTTACCCCAGACTGTGCAGATGTCCTAATACATAGCACTTATTTCCCTTGCTTTA

5200
    AlaGlyGluValArgArgAlaIleArgGlyGluLysLeuLeuSerCysCysAsnTyrPro
  CAGCAGGTGAAGTAAGAAGAGCCATCAGAGGGGAAAAGTTATTGTCCTGCTGCAATTATC

ArgAlaHisArgAlaGlnValProSerLeuGlnPheLeuAlaLeuValValValGlnGln
  CCCGAGCTCATAGACCCCAGGTACCGTCACTTCAATTTCTGGCCTTAGTGGTAGTCCAAC

5300
    MetThrAspProArgGluThrValProProGlyAsnSerGlyGluGluThrIleGly
    AsnAspArgProGlnArgAspSerThrThrArgLysGlnArgArgArgAspTyrArgArg
  AAAATGACAGACCCCAGAGAGACAGTACCACCAGGAAACAGCGGCGAAGAGACTATCGGA

5400
  GluAlaPheAlaTrpLeuAsnArgThrValGluAlaIleAsnArgGluAlaValAsnHis
    GlyLeuArgLeuAlaLysGlnAspSerArgSerHisLysGlnArgSerSerGluSerPro
  GAGGCCTTCGCCTGGCTAAACAGGACAGTAGAAGCCATAAACAGAGAAGCAGTGAATCAC

LeuProArgGluLeuIlePheGlnValTrpGlnArgSerTrpArgTyrTrpHisAspGlu
    ThrProArgThrTyrPheProGlyValAlaGluValLeuGluIleLeuAla
  CTACCCCGAGAACTTATTTTCCAGGTGTGGCAGAGGTCCTGGAGATACTGGCATGATGAA

5500
  GlnGlyMetSerGluSerTyrThrLysTyrArgTyrLeuCysIleIleGlnLysAlaVal
  CAAGGGATGTCAGAAAGTTACACAAAGTATAGATATTTGTGCATAATACAGAAAGCAGTG

TyrMetHisValArgLysGlyCysThrCysLeuGlyArgGlyHisGlyProGlyGlyTrp
  TACATGCATGTTAGGAAAGGGTGTACTTGCCTGGGGAGGGGACATGGGCCAGGAGGGTGG

5600
ArgProGlyProProProProProProProGlyLeuVal
                                          MetAlaGluAlaProThrGlu
  AGACCAGGGCCTCCTCCTCCTCCCCCTCCAGGTCTGGTCTAATGGCTGAAGCACCAACAG

5700
    LeuProProValAspGlyThrProLeuArgGluProGlyAspGluTrpIleIleGluIle
  AGCTCCCCCCGGTGGATGGGACCCCACTGAGGGAGCCAGGGGATGAGTGGATAATAGAAA

LeuArgGluIleLysGluGluAlaLeuLysHisPheAspProArgLeuLeuIleAlaLeu
  TCTTGAGAGAAATAAAAGAAGAAGCTTTAAAGCATTTTGACCCTCGCTTGCTAATTGCGC

5800
                      MetGluThrProLeuLysAlaProGluSerSerLeu
    GlyLysTyrIleTyrThrArgHisGlyAspThrLeuGluGlyAlaArgGluLeuIleLys
  TTGGCAAATATATCTATACTAGACATGGAGACACCCTTGAAGGCGCCAGAGAGCTCATTA

LysSerCysAsnGluProPheSerArgThrSerGluGlnAspValAlaThrGlnGluLeu
    ValLeuGlnArgAlaLeuPheThrHisPheArgAlaGlyCysGlyHisSerArgIleGly
  AAGTCCTGCAACGAGCCCTTTTCACGCACTTCAGAGCAGGATGTGGCCACTCAAGAATTG

5900
  AlaArgGlnGlyGluGluIleLeuSerGlnLeuTyrArgProLeuGluThrCysAsnAsn
    GlnThrArgGlyGlyAsnProLeuSerAlaIleProThrProArgAsnMetGln
  GCCAGACAAGGGGAGGAAATCCTCTCTCAGCTATACCGACCCCTAGAAACATGCAATAAC
```

-continued

```
                                                        6000
SerCysTyrCysLysArgCycCysTyrHisCysGlnMetCysPheLeuAsnLysGlyLeu
TCATGCTATTGTAAGCGATGCTGCTACCATTGTCAGATGTGTTTTCTAAACAAGGGGCTC

GlyIleCysTyrGluArgLysGlyArgArgArgThrProLysCysThrLysThrHis
         MetAsnGluArgAlaAspGluGluGlyLeuGlnArgLysLeuArgLeuIle
GGGATATGTTATGAACGAAAGGGCAGACGAAGAAGGACTCCAAAGAAAACTAAGACTCAT
                                6100
ProSerProThrProAspLys
 ArgLeuLeuHisGlnThr
                          MetMetAsnGlnLeuLeuIleAlaIleLeuLeuAla
CCGTCTCCTACACCAGACAAGTGAGTATGATGAATCAGCTGCTTATTGCCATTTTATTAG

SerAlaCysLeuValTyrCysThrGlnTyrValThrValPheTyrGlyValProThrTrp
CTAGTGCTTGCTTAGTATATTGCACCCAATATGTAACTGTTTTCTATGGCGTACCCACGT

6200
   LysAsnAlaThrIleProLeuPheCysAlaThrArgAsnArgAspThrTrpGlyThrIle
GGAAAAATGCAACCATTCCCCTCTTTTGTGCAACCAGAAATAGGGATACTTGGGGAACCA

6300
   GlnCysLeuProAspAsnAspAspTyrGlnGluIleThrLeuAsnValThrGluAlaPhe
TACAGTGCTTGCCTGACAATGATGATTATCAGGAAATAACTTTGAATGTAACAGAGCCTT

AspAlaTrpAsnAsnThrValThrGluGlnAlaIleGluAspValTrpHisLeuPheGlu
TTGATGCATGGAATAATACAGTAACAGAACAAGCAATAGAAGATGTCTGGCATCTATTCG

6400
   ThrSerIleLysProCysValLysLeuThrProLeuCysValAlaMetLysCysSerSer
AGACATCAATAAAACCATGTGTCAAACTAACACCTTTATGTGTAGCAATGAAATGCAGCA

ThrGluSerSerThrGlyAsnAsnThrThrSerLysSerThrSerThrThrThrThrThr
GCACAGAGAGCAGCACAGGGAACAACACAACCTCAAAGAGCACAAGCACAACCACAACCA

6500
   ProThrAspGlnGluGlnGluIleSerGluAspThrProCysAlaArgAlaAspAsnCys
CACCCACAGACCAGGAGCAAGAGATAAGTGAGGATACTCCATGCGCACGCGCAGACAACT

6600
   SerGlyLeuGlyGluGluGluThrIleAsnCysGlnPheAsnMetThrGlyLeuGluArg
GCTCAGGATTGGGAGAGGAAGAAACGATCAATTGCCAGTTCAATATGACAGGATTAGAAA

AspLysLysLysGlnTyrAsnGluThrTrpTyrSerLysAspValValCysGluThrAsn
GAGATAAGAAAAAACAGTATAATGAAACATGGTACTCAAAAGATGTGGTTTGTGAGACAA

6700
   AsnSerThrAsnGlnThrGlnCysTyrMetAsnHisCysAsnThrSerValIleThrGlu
ATAATAGCACAAATCAGACCCAGTGTTACATGAACCATTGCAACACATCAGTCATCACAG

SerCysAspLysHisTyrTrpAspAlaIleArgPheArgTyrCysAlaProProGlyTyr
AATCATGTGACAAGCACTATTGGGATGCTATAAGGTTTAGATACTGTGCACCACCGGGTT

6800
   AlaLeuLeuArgCysAsnAspThrAsnTyrSerGlyPheAlaProAsnCysSerLysVal
ATGCCCTATTAAGATGTAATGATACCAATTATTCAGGCTTTGCACCCAACTGTTCTAAAG

6900
   ValAlaSerThrCysThrArgMetMetGluThrGlnThrSerThrTrpPheGlyPheAsn
TAGTAGCTTCTACATGCACCAGGATGATGGAAACGCAAACTTCCACATGGTTTGGCTTTA

GlyThrArgAlaGluAsnArgThrTyrIleTyrTrpHisGlyArgAspAsnArgThrIle
ATGGCACTAGAGCAGAGAATAGAACATATATCTATTGGCATGGCAGAGATAATAGAACTA

7000
   IleSerLeuAsnLysTyrTyrAsnLeuSerLeuHisCysLysArgProGlyAsnLysThr
TCATCAGCTTAAACAAATATTATAATCTCAGTTTGCATTGTAAGAGGCCAGGGAATAAGA

ValLysGlnIleMetLeuMetSerGlyHisValPheHisSerHisTyrGlnProIleAsn
CAGTGAAACAAATAATGCTTATGTCAGGACATGTGTTTCACTCCCACTACCAGCCGATCA

7100
   LysArgProArgGlnAlaTrpCysTrpPheLysGlyLysTrpLysAspAlaMetGlnGlu
```

```
                                              -continued
ATAAAAGACCCAGACAAGCATGGTGCTGGTTCAAAGGCAAATGGAAAGACGCCATGCAGG .         .         .         .         .       7200
   ValLysGluThrLeuAlaLysHisProArgTyrArgGlyThrAsnAspThrArgAsnIle
AGGTGAAGGAAACCCTTGCAAAACATCCCAGGTATAGAGGAACCAATGACACAAGGAATA .         .         .         .         .         .
   SerPheAlaAlaProGlyLysGlySerAspProGluValAlaTyrMetTrpThrAsnCys
TTAGCTTTGCAGCGCCAGGAAAAGGCTCAGACCCAGAAGTAGCATACATGTGGACTAACT .         .       7300        .         .         .
   ArgGlyGluPheLeuTyrCysAsnMetThrTrpPheLeuAsnTrpIleGluAsnLysThr
GCAGAGGAGAGTTTCTCTACTGCAACATGACTTGGTTCCTCAATTGGATAGAGAATAAGA .         .         .         .         .         .
   HisArgAsnTyrAlaProCysHisIleLysGlnIleIleAsnThrTrpHisLysValGly
CACACCGCAATTATGCACCGTGCCATATAAAGCAAATAATTAACACATGGCATAAGGTAG .       7400        .         .         .         .
   ArgAsnValTyrLeuProProArgGluGlyGluLeuSerCysAsnSerThrValThrSer
GGAGAAATGTATATTTGCCTCCCAGGGAAGGGGAGCTGTCCTGCAACTCAACAGTAACCA .         .         .         .       7500        .
   IleIleAlaAsnIleAspTrpGlnAsnAsnAsnGlnThrAsnIleThrPheSerAlaGlu
GCATAATTGCTAACATTGACTGGCAAAACAATAATCAGACAAACATTACCTTTAGTGCAG .         .         .         .         .         .
   ValAlaGluLeuTyrArgLeuGluLeuGlyAspTyrLysLeuValGluIleThrProIle
AGGTGGCAGAACTATACAGATTGGAGTTGGGAGATTATAAATTGGTAGAAATAACACCAA .         .         .       7600        .         .
   GlyPheAlaProThrLysGluLysArgTyrSerSerAlaHisGlyArgHisThrArgGly
TTGGCTTCGCACCTACAAAAGAAAAAAGATACTCCTCTGCTCACGGGAGACATACAAGAG .         .         .         .         .         .
   ValPheValLeuGlyPheLeuGlyPheLeuAlaThrAlaGlySerAlaMetGlyAlaAla
GTGTGTTCGTGCTAGGGTTCTTGGGTTTTCTCGCAACAGCAGGTTCTGCAATGGGCGCGG .       7700        .         .         .         .
   SerLeuThrValSerAlaGlnSerArgThrLeuLeuAlaGlyIleValGlnGlnGlnGln
CGTCCCTGACCGTGTCGGCTCAGTCCCGGACTTTACTGGCCGGGATAGTGCAGCAACAGC .         .         .         .       7800        .
   GlnLeuLeuAspValValLysArgGlnGlnGluLeuLeuArgLeuThrValTrpGlyThr
AACAGCTGTTGGACGTGGTCAAGAGACAACAAGAACTGTTGCGACTGACCGTCTGGGGAA .         .         .         .         .         .
   LysAsnLeuGlnAlaArgValThrAlaIleGluLysTyrLeuGlnAspGlnAlaArgLeu
CGAAAAACCTCCAGGCAACAGTCACTGCTATAGAGAAGTACCTACAGGACCAGGCGCGGC .         .         .       7900        .         .
   AsnSerTrpGlyCysAlaPheArgGlnValCysHisThrThrValProTrpValAsnAsp
TAAATTCATGGGGATGTGCGTTTAGACAAGTCTGCCACACTACTGTACCATGGGTTAATG .         .         .         .         .         .
   SerLeuAlaProAspTrpAspAsnMetThrTrpGlnGluTrpGluLysGlnValArgTyr
ATTCCTTAGCACCTGACTGGGACAATATGACGTGGCAGGAATGGGAAAAACAAGTCCGCT .       8000        .         .         .         .
   LeuGluAlaAsnIleSerLysSerLeuGluGlnAlaGlnIleGlnGlnGluLysAsnMet
ACCTGGAGGCAAATATCAGTAAAAGTTTAGAACAGGCACAAATTCAGCAAGAGAAAAATA .         .         .         .       8100        .
   TyrGluLeuGlnLysLeuAsnSerTrpAspIlePheGlyAsnTrpPheAspLeuThrSer
TGTATGAACTACAAAAATTAAATAGCTGGGATATTTTTGGCAATTGGTTTGACTTAACCT .         .         .         .         .         .
   TrpValLysTyrIleGlnTyrGlyValLeuIleIleValAlaValIleAlaLeuArgIle
CCTGGGTCAAGTATATTCAATATGGAGTCCTTATAATAGTAGCAGTAATAGCTTTAACAA .         .         .       8200        .         .
   ValIleTyrValValGlnMetLeuSerArgLeuArgLysGlyTyrArgProValPheSer
TAGTGATATATGTAGTACAAATGTTAAGTAGGCTTAGAAAGGGCTATAGGCCTGTTTTCT .         .                 SerIleSerThrArgThrGlyAspSerGlnPro
                           AsnProTyrProGlnGlyProGlyThrAlaSerGln
   SerProProGlyTyrIleGlnGlnIleHisIleHisLysAspArgGlyGlnProAlaAsn
CTTCCCCCCCCGGTTATATCCAACAGATCCATATCCACAAGGACCGGGGACAGCCAGCCA

.       8300        .         .         .         .
```

-continued

```
ThrLysLysGlnLysLysThrValGluAlaThrValGluThrAspThrGlyProGlyArg
 ArgArgAsnArgArgArgArgTrpLysGlnArgTrpArgGlnIleLeuAlaLeuAlaAsp
  GluGluThrGluGluAspGlyGlySerAsnGlyGlyAspArgTyrTrpProTrpProIle
ACGAAGAAACAGAAGAAGACGGTGGAAGCAACGGTGGAGACAGATACTGGCCCTGGCCGA
                                           .         8400
    SerIleTyrThrPheProAspProProAlaAspSerProLeuAspGlnThrIleGlnHis
     AlaTyrIleHisPheLeuIleArgGlnLeuIleArgLeuLeuThrArgLeuTyrSerIle
TAGCATATATACATTTCCTGATCCGCCAGCTGATTCGCCTCTTGACCAGACTATACAGCA

LeuGlnGlyLeuThrIleGlnGluLeuProAspProProThrHisLeuProGluSerGln
      CysArgAspLeuLeuSerArgSerPheLeuThrLeuGlnLeuIleTyrGlnAsnLeuArg
TCTGCAGGGACTTACTATCCAGGAGCTTCCTGACCCTCCAACTCATCTACCAGAATCTCA

.         8500         .
 ArgLeuAlaGluThr              MetGlyAlaSerGlySerLysLys
    AspTrpLeuArgLeuArgThrAlaPheLeuGlnTyrGlyCysGluTrpIleGlnGluAla
GAGACTGGCTGAGACTTAGAACAGCCTTCTTGCAATATGGGTGCGAGTGGATCCAAGAAG

HisSerArgProProArgGlyLeuGlnGluArgLeuLeuArgAlaArgAlaGlyAlaCys
  PheGlnAlaAlaAlaArgAlaThrArgGluThrLeuAlaGlyAlaCysArgGlyLeuTrp
CATTCCAGGCCGCCGCGAGGGCTACAAGAGAGACTCTTGAGGGCGCGTGCAGGGGCTTCT

.         8600         .         .         .
GlyGlyTyrTrpAsnGluSerGlyGluGluTyrSerArgPheGlnGluGlySerAspArg
    ArgValLeuGluArgIleGlyArgGlyIleLeuAlaValProArgArgIleArgGlnGly
GCAGCGTATTGGAACGAATCGGAGGGGAATACTCGCGGTTCCAAGAAGGATCAGACAGC

.         .         8700
GluGlnLysSerProSerCysGluGlyArgGlnTyrGlnGlnGlyAspPheMetAsnThr
    AlaGluIleAlaLeuLeu
GAGCAGAAATCGCCCTCCTGTGAGGGACGGCAGTATCAGCAGGGAGACTTTATGAATACT

ProTrpLysAspProAlaAlaGluArgGluLysAsnLeuTyrArgGlnGlnAsnMetAsp
CCATGGAAGGACCCAGCAGCAGAAAGGGAGAAAAATTTGTACAGGCAACAAAATATGGAT

.         .         8800         .         .
AspValAspSerAspAspAspAspGlnValArgValSerValThrProLysValProLeu
GATGTAGATTCAGATGATGATGACCAAGTAAGAGTTTCTGTCACACCAAAAGTACCACTA

ArgProMetThrHisArgLeuAlaIleAspMetSerHisLeuIleLysThrArgGlyGly
AGACCAATGACACATAGATTGGCAATAGATATGTCACATTTAATAAAAACAAGGGGGGA

.         8900         .         .         .         .
LeuGluGlyMetPheTyrSerGluArgArgHisLysIleLeuAsnIleTyrLeuGluLys
CTGGAAGGGATGTTTTACAGTGAAAGAAGACATAAAATCTTAAATATATACTTAGAAAAG

.         9000
GluGluGlyIleIleAlaAspTrpGlnAsnTyrThrHisGlyProGlyValArgTyrPro
CAAGAAGGGATAATTGCAGATTGGCAGAACTACACTCATGGGCCAGGAGTAAGATACCCA

MetPhePheGlyTrpLeuTrpLysLeuValProValAspValProGlnGluGlyGluAsp
ATGTTCTTTGGGTGGCTATGGAAGCTAGTACCAGTAGATGTCCCACAAGAAGGGGAGGAC

.         9100         .         .
ThrGluThrHisCysLeuValHisProAlaGlnThrSerLysPheAspAspProHisGly
ACTGAGACTCACTGCTTAGTACATCCAGCACAAACAAGCAAGTTTGATGACCCGCATGGG

GluThrLeuValTrpGluPheAspProLeuLeuAlaTyrSerTyrGluAlaPheIleArg
GAGACACTAGTCTGGGAGTTTGATCCCTTGCTGGCTTATAGTTACGAGGCTTTTATTCGG

.         9200         .         .         .         .
TyrProGluGluPheGlyHisLysSerGlyLeuProGluGluGluTrpLysAlaArgLeu
TACCCAGAGGAATTTGGGCACAAGTCAGGCCTGCCAGAGGAAGAGTGGAAGGCGAGACTG

.         9300
LysAlaArgGlyIleProPheSer
AAAGCAAGAGCAATACCATTTAGTTAAAGACAGGAACAGCTATACTTGGTCAGGGCAGGA

AGTAACTAACAGAAACAGCTGAGACTGCAGGGACTTTCCAGAAGGGGCTGTAACCAAGGG

.         9400         .         .
AGGGACATGGGAGGAGCTGGTGGGAACGCCCTCATATTCTCTGTATAAATATACCCGCT
```

```
AGCTTGCATTGTACTTCGGTCGCTCTGCGGAGAGGCTGGCAGATTGAGCCCTGGGAGGTT

9500
CTCTCCAGCAGTAGCAGGTAGAGCCTGGGTGTTCCCTGCTAGACTCTCACCAGCACTTGG

9600
CCGGTGCTGGGCAGACGGCCCCACGCTTGCTTGCTTAAAAACCTCCTTAATAAAGCTGCC

AGTTAGAAGCA
```

Example 5: Sequences of the coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

Envelope sequence

```
Envelope sequence

MetMetAsnGlnLeuLeuIleAlaIleLeuLeuAlaSerAlaCys
ATGATGATCCAGCTGCTTATTGCCATTTTATTAGCTAGTGCTTGC

.         .         .         .
LeuValTyrCysThrGlnTyrValThrValPheTyrGlyValPro
TTAGTATATTGCACCCAATATGTAACTGTTTTCTATGGCGTACCC

.         .         .         .         .
ThrTrpLysAsnAlaThrIleProLeuPheCysAlaThrArgAsn
ACGTGGAAAAATGCAACCATTCCCCTGTTTTGTGCAACCAGAAAT
       100              .         .         .
ArgAspThrTrpGlyThrIleGlnCysLeuProAspAsnAspAsp
AGGGATACTTGGGGAACCATACAGTGCTTGCCTGACAATGATGAT

.         .         .         .         .
TyrGlnGluIleThrLeuAsnValThrGluAlaPheAspAlaTrp
TATCAGGAAATAACTTTGAATGTAACAGAGGCTTTTGATGCATGG
          .      200            .         .
AsnAsnThrValThrGluGlnAlaIleGluAspValTrpHisLeu
AATAATACAGTAACAGAACAAGCAATAGAAGATGTCTGGCATCTA

.         .         .         .         .
PheGluThrSerIleLysProCysValLysLeuThrProLeuCys
TTCGAGACATCAATAAAACCATGTGTGAAACTAACACCTTTATGT
          .         .      300            .
ValAlaMetLysCysSerSerThrGluSerSerThrGlyAsnAsn
GTAGCAATGAAATGCAGCAGCACAGAGAGCAGCACAGGGAACAAC

.         .         .         .         .
ThrThrSerLysSerThrSerThrThrThrThrThrProThrAsp
ACAACCTCAAAGAGCACAAGCACAACCACAACCACACCCAGAGAG
          .         .         .      400
GlnGluGlnGluIleSerGluAspThrProCysAlaArgAlaAsp
CAGGAGCAAGAGATAAGTGAGGATACTCCATGCGCACGCGCAGAC

.         .         .         .         .
AsnCysSerGlyLeuGlyGluGluGLuThrIleAsnCysGlnPhe
AACTGCTCAGGATTGGGAGAGGAAGAAACGATCAATTGCCAGTTC

.         .         .         .
AsnMetThrGlyLeuGluArgAspLysLysLysGlnTyrAsnGlu
AATATGACAGGATTAGAAAGAGATAAGAAAAAACAGTATAATGAA
   500             .         .         .         .
ThrTrpTyrSerLysAspValValCysGluThrAsnAsnSerThr
ACATGGTACTCAAAAGATGTGGTTTGTGAGACAAATAATAGCACA

.         .         .         .
AsnGlnThrGlnCysTyrMetAsnHisCysAsnThrSerValIle
AATCAGACCCAGTGTTACATGAACCATTGCAACACATCAGTCATC
     .      600             .         .         .
ThrGluSerCysAspLysHisTyrTrpAspAlaIleArgPheArg
ACAGAATCATGTGACAAGCACTATTGGGATGCTATAAGGTTTAGA

.         .         .         .
TyrCysAlaProProGlyTyrAlaLeuLeuArgCysAsnAspThr
```

-continued

```
TACTGTGCACCACCGGGTTATGCCCTATTAAGATGTAATGATACC
     .         .      700            .         .
AsnTrySerGlyPheAlaProAsnCysSerLysValValAlaSer
AATTATTCAGGCTTTGCACCCAACTGTTCTAAAGTAGTAGCTTCT

.         .         .         .
ThrCysThrArgMetMetGluThrGlnThrSerThrTrpPheGly
ACATGCACCAGGATGATGGAAACGCAAACTTCCACATGGTTTGGC
     .         .         .      800            .
PheAsnGlyThrArgAlaGluAsnArgThrTyrIleTyrTrpHis
TTTAATGGCACTAGAGCAGAGAATAGAACATATATCTATTGGCAT

.         .         .         .
GlyArgAspAsnArgThrIleIleSerLeuAsnLysTyrTyrAsn
GGCAGAGATAATAGAACTATCATCAGCTTAAACAAATATTATAAT
     .         .         .         .      900
LeuSerLeuHisCysLysArgProGlyAsnLysThrValLysGln
CTCAGTTTGCATTGTAAGAGGCCAGGGAATAAGACAGTGAAACAA

.         .         .         .
IleMetLeuMetSerGlyHisValPheHisSerHisTyrGlnPro
ATAATGCTTATGTCAGGACATGTGTTTCACTCCCACTACCAGCCG

.         .         .         .         .
IleAsnLysArgProArgGlnAlaTrpCysTrpPheLysGluLys
ATCAATAAAAGACCCAGACAAGCATGGTGCTGGTTCAAAGGCAAA
      1000          .         .         .
TrpLysAspAlaMetGlnGluValLysThrLeuAlaLysHisPro
TGGAAAGACGCCATGCAGGAGGTGAAGACCCTTGCAAAACATCCC

.         .         .         .         .
ArgTyrArgGlyThrAsnAspThrArgAsnIleSerPheAlaAla
AGGTATAGAGGAACCAATGACACAAGGAATATTAGCTTTGCAGCG
          .      1100           .         .
ProGlyLysGlySerAspProGluValAlaTyrMetTrpThrAsn
CCAGGAAAAGGCTCAGACCCAGAAGTAGCATACATGTGGACTAAC

.         .         .         .         .
CysArgGlyGluPheLeuTyrCysAsnMetThrTrpPheLeuAsn
TGCAGAGGAGAGTTTCTCTACTGCAACATGACTTGGTTCCTCAAT
          .         .      1200           .
TrpIleGluAsnLysThrHisArgAsnTyrAlaProCysHisIle
TGGATAGAGAATAAGACACACCGCAATTATGCACCGTGCCATATA

.         .         .         .         .
LysGlnIleIleAsnThrTrpHisLysValGlyArgAsnValTyr
AAGCAAATAATTAACACATGGCATAAGGTAGGGAGAAATGTATAT
          .         .         .      1300
LeuProProArgGluGlyGluLeuSerCysAsnSerThrValThr
TTGCCTCCCAGGGAAGGGGAGCTGTCCTGCAACTCAACAGTAACC

.         .         .         .         .
SerIleIleAlaAsnIleAspTrpGlnAsnAsnAsnGlnThrAsn
AGCATAATTGCTAACATTGACTGGCAAAACAATAATCAGACAAAC

.         .         .         .
IleThrPheSerAlaGluValAlaGluLeuTyrArgLeuGluLeu
ATTACCTTTAGTGCAGAGGTGGCAGAACTATACAGATTGGAGTTG
 1400              .         .         .         .
GlyAspTyrLysLeuValGluIleThrProIleGlyPheAlaPro
GGAGATTATAAATTGGTAGAAATAACACCAATTGGCTTCGCACCT

.         .         .         .
ThrLysGluLysArgTyrSerSerAlaHisGlyArgHisThrArg
ACAAAAGAAAAAAGATACTCCTCTGCTCACGGGAGACATACAAGA
     .     1500            .         .         .
GlyValPheValLeuGlyPheLeuGlyPheLeuAlaThrAlaGly
GGTGTGTTCGTGCTAGGGTTCTTGGGTTTTCTCGCAACAGCAGGT

.         .         .         .
SerAlaMetGlyAlaArgAlaSerLeuThrValSerAlaGlnSer
TCTGCAATGGGCGCTCGAGCGTCCCTGACCGTGTCGGCTCAGTCC
     .         .      1600           .         .
ArgThrLeuLeuAlaGlyIleValGlnGlnGlnGlnGlnLeuLeu
CGGACTTTACTGGCCGGGATAGTGCAGCAACAGCAACAGCTGTTG
```

-continued

```
AspValValLysArgGlnGlnGluLeuLeuArgLeuThrValTrp
GACGTGGTCAAGAGACAACAAGAACTGTTGCGACTGACCGTCTGG
                    .         .         1700
GlyThrLysAsnLeuGlnAlaArgValThrAlaIleGluLysTyr
GGAACGAAAAACCTCCAGGCAAGAGTCACTGCTATAGAGAAGTAG

LeuGluGlnAlaArgLeuAsnSerTrpGlyCysAlaPheArg
CTACAGGACCAGGCGCGGCTAAATTCATGGGGATGTGCGTTTAGA
                    .         .         1800
GlnValCysHisThrThrValProTrpValAsnAspSerLeuAla
CAAGTCTGCCACACTACTGTACCATGGGTTAATGATTCCTTAGCA

ProAspTrpAspAsnMetThrTrpGlnGluTrpGluLysGlnVal
CCTGACTGGGACAATATGACGTGGCAGGAATCCCAAAACAAGTC

ArgTyrLeuGluAlaAsnIleSerLysSerLeuGluGlnAlaGln
CGCTACCTGGAGGCAAATATCAGTAAAAGTTTAGAACAGGCACAA
          1900          .         .
IleGlnGlnGluLysAsnMetTyrGluLeuGlnLysLeuAsnSer
ATTCAGCAAGAGAAAAATATGTATGAACTACAAAAATTAAATAGC

TrpAspIlePheGlyAsnTrpPheAspLeuThrSerTrpValLys
TGGGATATTTTTGGCAATTGGTTTGACTTAACCTCCTGGGTCAAG
                    .         .         2000
TyrIleGlnTyrGlyValLeuIleIleValAlaValIleALaLeu
TATATTCAATATGGAGTGCTTATAATAGTAGCAGTAATAGCTTTA

ArgIleValIleTyrValValGlnMetLeuSerArgLeuArgLys
AGAATAGTGATATATGTAGTACAAATGTTAAGTAGGCTTAGAAAG
                    .         .         2100
GlyTyrArgProValPheSerSerProProGlyTyrIleGln***
GGCTATAGGCCTGTTTTCTCTTCCCCCCCCGGTTATATCCAATAG

IleHisIleHisLysAspArgGlyGlnProAlaAsnGluGluThr
ATCCATATCCACAAGGACCGGGGACAGCCAGCCAACGAAGAAACA
                    .         .         2200
GluGluAspGlyGlySerAsnGlyGlyAspArgTyrTrpProTrp
CAAGAAGACGGTGGAAGCAACGGTGGAGACACATACTGGCCCTGG

ProIleAlaTyrIleHisPheLeuIleArgGlnLeuIleArgLeu
GCGATAGCATATATACATTTCCTGATCCGCCAGCTGATTCGCCTC

LeuThrArgLeuTyrSerIleCysArgAspLeuLeuSerArgSer
TTGACCAGACTATACAGCATCTGCAGGGACTTACTATCCAGGAGC
          2300          .         .
PheLeuThrLeuGlnLeuIleTyrGlnAsnLeuArgAspTrpLeu
CTCCTGACCCTCCAACTCATCTACCAGAATCTCAGAGACTGGCTG

ArgLeuArgThrAlaPheLeuGluTyrGlyCysGluTrpIleGln
AGACTTAGAACAGCCTTCTTGCAATATGGGTGCGAGTGGATCCAA
                    .         .         2400
GluAlaPheGlnAlaAlaAlaArgAlaThrArgGluThrLeuAla
GAAGCATTCCAGGCCGCCGCGAGGGCTACAAGAGAGACTCTTGCG

GlyAlaCysArgGlyLeuTrpArgValLeuGluArgIleGlyArg
GGCGCGTGCAGGGGCTTGTGGAGGGTATTGGAACGAATCGGGAGG
                    2500          .         .
GlyIleLeuAlaValProArgArgIleArgGlnGlyAlaGluIle
CGAATACTCGCGGTTCCAAGAAGGATCAGACAGGGAGCAGAAATC

AlaLeuLeu***GlyThrAlaValSerAlaGlyArgLeuTyrGlu
GCCCTCCTGTGAGGGACGGCAGTATCAGCAGGGAGACTTTATGAA
                    .         .         2600
TyrSerMetGluGlyProSerSerArgLysGlyGluLysPheVal
TACTCCATGGAAGGACCCAGCAGCAGAAAGGGAGAAAAATTTGTA

GlnAlaThrLysTyrGly
GAGGCAACAAAATATGGA

Gag sequence

MetGlyAlaArgAsnSerValLeuArgGlyLysLysAlaAspGlu
ATGGGCGCGAGAAACTCCGTCTTGAGGGGAAAAAAGCAGATGAA

LeuGluArgIleArgLeuArgProGlyGlyLysLysLysTyrArg
TTAGAAAGAATCAGGTTACGGCCCGGCGGAAAGAAAAAGTACAGG
```

```
LeuLysHisIleValTrpAlaAlaAsnLysLeuAspArgPheGly
CTAAAACATATTGTGTGGGCAGCGAATAAATTGGACAGATTCGGA
          100          .         .
LeuAlaGluSerLeuLeuGluSerLysGluGlyCysGluLysIle
TTAGCAGAGAGCCTGTTGGAGTCAAAAGAGGGTTGTCAAAAAATT

LeuThrValLeuAspProMetValProThrGlySerGluAsnLeu
CTTACAGTTTTAGATCCAATGGTACCGACAGGTTCAGAAAATTTA
          200          .         .
LysSerLeuPheAsnThrValCysValIleTrpCysIleHisAla
AAAAGTCTTTTTAATACTGTCTGCGTCATTTGGTGCATACACGCA

GluGluLysValLysAspThrGluGlyAlaLysGlnIleValArg
GAAGAGAAAGTGAAAGATACTGAAGGAGCAAAACAAATAGTGCGG
                    300          .
ArgHisLeuValAlaGluThrGlyThrAlaGluLysMetProSer
AGACATCTAGTGGCAGAAACAGGAACTGCAGAGAAAATGCCAAGG

ThrSerArgProThrAlaProSerSerGluLysGlyGlyAsnTyr
ACAAGTAGACCAACAGCACCATCTAGCGAGAAGGGAGGAAATTAC
                    .         .         400
ProValGlnHisValGlyGlyAsnTyrThrHisIleProLeuSer
CCAGTGCAACATGTAGGCGGCAACTACACCCATATACCGCTGAGT

ProArgThrLeuAsnAlaTrpValLysLeuValGluGluLysLys
CCCCGAACCCTAAATGCCTGGGTAAAATTAGTAGAGGAAAAAAAG

PheGlyAlaGluValValProGlyPheGluAlaLeuSerGluGly
TTCGGGGCAGAAGTAGTGCCAGGATTTCAGGCACTCTCAGAAGGC
          500
CysThrProTyrAspIleAsnGlnMetLeuAsnCysValGlyAsp
TGGACGCCCTATGATATCAACCAAATGCTTAATTGTGTGGGCGAC

HisGlnAlaAlaMetGlnIleIleArgGluIleIleAsnGluGlu
CATCAAGCAGCCATGCAGATAATCAGGGAGATTATCAATGAGGAA
                    600          .
AlaAlaGluTrpAspValGlnHisProIleProGlyProLeuPro
GCAGCAGAATGGGATGTGCAACATCCAATACCAGCCCCCTTAGCA

AlaGlyGlnLeuArgGluProArgGlySerAspIleAlaGlyThr
GCGGGGCAGCTTAGAGAGCCAAGGGGATCTGACATAGCAGGGACA
                    .         .         700
ThrSerThrValGluGluGlnIleGlnTrpMetPheArgProGln
ACAAGCACAGTAGAAGAACAGATCCAGTGGATGTTTAGGCCACAA

AsnProValProValGlyAsnIleTyrArgArgTrpIleGlnIle
AATCCTGTACCAGTAGGAAACATCTATAGAAGATGGATCCAGATA
                    .         .         800
GlyLeuGlnLysCysValArgMetTyrAsnProThrAsnIleLeu
GGATTGCAGAAGTGTGTCAGGATGTACAACCCGACCAACATCCTA

AspIleLysGlnGlyProLysGluProPheGlnSerTyrValAsp
GACATAAAACAGGGACCAAAGGAGCCGTTCCAAAGCTATGTAGAT
                    .         .         900
ArgPheTyrLysSerLeuArgAlaGluGlnThrAspProAlaVal
AGATTCTACAAAAGCTTGAGGGCAGAACAAACAGATCCAGCAGTG

LysAsnTrpMetThrGlnThrLeuLeuValGlnAsnAlaAsnPro
AAGAATTGGATGACCCAAACACTGCTAGTACAAAATGCCAACCCA

AspCysLysLeuValLeuLysGlyLeuGlyMetAsnProThrLeu
GACTGTAAATTAGTGCTAAAAGGACTAGGGATGAACCCTACCTTA
          1000
GluGluMetLeuThrAlaCysGlnGlyValGlyGlyProGlyGln
GAAGAGATGCTGACCGCCTGTCAGGGGGTAGGTGGGCCAGGCCAG

LysAlaArgLeuMetAlaGluAlaLeuLysGluValIleGlyPro
AAAGCTAGATTAATGGCAGAGGCCCTGAAAGAGGTCATAGGACCT
                    1100
AlaProIleProPheAlaAlaAlaGlnGlnArgLysAlaPheLys
GCCCCTATCCCATTCGCAGCAGCCCAGCAGAGAAAGGCATTTAAA

CysTrpAsnCysGlyLysGluGlyHisSerAlaArgGlnCysArg
TGCTGGAACTGTGGAAAGGAAGGGCACTCGGCAAGACAATGCCGA
                    .         .         1200
AlaProArgArgGlnGlyCysTrpLysCysGlyLysProGlyHis
GCACCTAGAAGGCAGGGCTGCTGGAAGTGTGGTAAGCCAGGACAC

IleMetThrAsnCysProAspArgGlnAlaGlyPheLeuGlyLeu
ATCATGACAAACTGCCCAGATAGACAGGCAGGTTTTTAGGACTG
                              1300
```

-continued
```
GlyProTrpGlyLysLysProArgAsnPheProValAlaGlnVal
GGCCCTTGGGGAAAGAAGCCCCGCAACTTCCCCGTGGCCCAAGTT
    .         .         .         .
ProGlnGlyLeuThrProThrAlaProProValAspProAlaVal
CCGCAGGGGCTGACACCAACAGCACCCCCAGTGGATCCAGCAGTG
    .         .         .         .
AspLeuLeuGluLysTyrMetGlnGlnGlyLysArgGlnArgGlu
GATCTACTGGAGAAATATATGCAGCAAGGGAAAAGACAGAGAGAG
1400      .         .         .
GlnArgGluArgProTyrLysGluValThrGluAspLeuLeuHis
CAGAGAGAGAGACCATACAAGGAAGTGACAGAGGACTTACTGCAC
    .         .         .         .
LeuGluGlnGlyGluThrProTyrArgGlnProProThrGluAsp
CTCGAGCAGGGGGAGACACCATACAGGGAGCCACCAACAGAGGAC
    .     1500      .         .
LeuLeuHisLeuAsnSerLeuPheGlyLysAspGln
TTGCTGCACCCTCAATTCTCTCTTTGGAAAAGACCAG
    .         .         .
```

Example 6: Peptide Sequences Encoded By The ENV and GAG genes

The following coding regions for antigenic peptides, identified for convenience only by the nucleotide numbers of Example 5, within the env and gag gene regions are of particular interest.

```
env1 (1732-1809)
                    ArgValThrAlaIleGluLysTyr
                    AGAGTCACTGCTATAGAGAAGTAC
              .
LeuGlnAspGlnAlaArgLeuAsnSerTrpGlyCysAlaPheArg
CTACAGGACCAGGCGCGGCTAAATTCATGGGGATGTGCGTTTAGA
    .         .         .         .    1800
GlnValCys
CAAGTCTGC env2 (1912-1983)
                    SerLysSerLeuGluGlnAlaGln
                    AGTAAAAGTTTAGAACAGGCACAA
                            .         .
IleGlnGlnGluLysAsnMetTyrGluLeuGlnLysLeuAsnSer
ATTCAGCAAGAGAAAAATATGTATGAACTACAAAAATTAAATAGC
1940      .         .         .         .
Trp
TGG env3 (1482-1530)
Pro ThrLysGluLysArgTyrSerSerAlaHisGlyArgHisThrArg
CCT ACAAAAGAAAAAGATACTCCTCTGCTCACGGGAGACATACAAGA
        .     1500      .         .         .

env4 (55-129)
          CysThrGlnTyrValThrValPheTyrGlyValPro
          TGCACCCAATATGTAACTGTTTTCTATGGCGTACCC
              .         .         .
ThrTrpLysAsnAlaThrIleProLeuPheCysAlaThr
ACGTGGAAAAATGCAACCATTCCCCTGTTTTGTGCAACC
    100       .         .         .

env5 (175-231)
                                        AspAsp
                                        GATGAT
                                            .
TyrGlnGlnIleThrLeuAsnValThrGluAlaPheAspAlaTrp
TATCAGGAAATAACTTTGAATGTAACAGAGGCTTTTGATGCATGG
    .     200       .         .
AsnAsn
AATAAT env6 (274-330)
    GluThrSerIleLysProCysValLysLeuThrProLeuCys
    GAGACATCAATAAAACCATGTGTGAAACTAACACCTTTATGT
        .         .     300       .
ValAlaMetLysCys
GTAGCAATGAAATGC
    .         .
```

-continued
```
env7 (607-660)
                        AsnHisCysAsnThrSerValIle
                        AACCATTGCAACACATCAGTCATC
                                610       .    .
ThrGluSerCysAspLysHisTyrTrpAsp
ACAGAATCATGTGACAAGCACTATTGGGAT
    .         .         .

env8 (661-720)
                            AlaIleArgPheArg
                            GCTATAAGGTTTAGA
                                  .
TyrCysAlaProProGlyTyrAlaLeuLeuArgCysAsnAspThr
TACTGTGCACCACCGGGTTATGCCCTATTAAGATGTAATGATACC
    .         .     700       .         .

env9 (997-1044)
        LysArgProArgGlnAlaTrpCysTrpPheLysGlyLys
        AAAAGACCCAGACAAGCATGGTGCTGGTTCAAAGGCAAA
        1000      .         .         .
TrpLysAsp
TGGAAAGAC env10 (1132-1215)
        LysGlySerAspProGluValAlaTyrMetTrpThrAsn
        AAAGGCTCAGACCCAGAAGTAGCATACATGTGGACTAAC
                .         .         .
CysArgGlyGluPheLeuTyrCysAsnMetThrTrpPheLeuAsn
TGCAGAGGAGAGTTTCTCTACTGCAACATGACTTGGTTCCTCAAT
    .         .     1200      .

env11 (1237-1305)
                        ArgAsnTyrAlaProCysHisIle
                        CGCAATTATGCACCGTGCCATATA
                              .         .
LysGlnIleIleAsnThrTrpHisLysValGlyArgAsnValTyr
AAGCAAATAATTAACACATGGCATAAGGTAGGGAGAAATGTATAT
    .         .         .    1300 gag1 (991-1053)
AspCysLysLeuValLeuLysGlyLeuGlyMetAsnProThrLeu
GACTGTAAATTAGTGCTAAAAGGACTAGGGATGAACCCTACCTTA
    1000      .         .         .
GluGluMetLeuThrAla
GAAGAGATGCTGACCGCC
    .         .
```

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the HIV group. For vaccinating purposes, the fore going peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | | DNA CODON | | | | AMINO ACID 3 LET. | | | | AMINO ACID 1 LET. | | | |
|---|---|---|---|---|---|---|---|---|---|---|---|---|---|
| | \2 | T | C | A | G | T | C | A | G | T | C | A | G |
| 1 | 3\ | | | | | | | | | | | | |
| | T | TTT | TCT | TAT | TGT | PHE | SER | TYR | CYS | F | S | Y | C |
| T | C | TTC | TCC | TAC | TGC | PHE | SER | TYR | CYS | F | S | Y | C |
| | A | TTA | TCA | TAA | TGA | LEU | SER | *** | *** | L | S | * | * |
| | G | TTG | TCG | TAG | TGG | LEU | SER | *** | TRP | L | S | * | W |
| | T | CTT | CCT | CAT | CGT | LEU | PRO | HIS | ARG | L | P | H | R |
| C | C | CTC | CCC | CAC | CGC | LEU | PRO | HIS | ARG | L | P | H | R |
| | A | CTA | CCA | CAA | CGA | LEU | PRO | GLN | ARG | L | P | Q | R |
| | G | CTG | CCG | CAG | CGG | LEU | PRO | GLN | ARG | L | P | Q | R |
| | T | ATT | ACT | AAT | AGT | ILE | THR | ASN | SER | I | T | N | S |
| A | C | ATC | ACC | AAC | AGC | ILE | THR | ASN | SER | I | T | N | S |
| | A | ATA | ACA | AAA | AGA | ILE | THR | LYS | ARG | I | T | K | R |
| | G | ATG | ACG | AAG | AGG | MET | THR | LYS | ARG | M | T | K | R |
| | T | GTT | GCT | GAT | GGT | VAL | ALA | ASP | GLY | V | A | D | G |
| G | C | GTC | GCC | GAC | GGC | VAL | ALA | ASP | GLY | V | A | D | G |
| | A | GTA | GCA | GAA | GGA | VAL | ALA | GLU | GLY | V | A | E | G |
| | G | GTG | GCG | GAG | GGG | VAL | ALA | GLU | GLY | V | A | E | G |

| 3 Letter | 1 Letter | CODONS |
|---|---|---|
| ALA | A | GCT GCC GCA GCG |
| ARG | R | CGT CGC CGA CGG AGA AGG |
| ASN | N | AAT AAC |
| ASP | D | GAT GAC |
| CYS | C | TGT TCC |
| GLN | Q | CAA CAG |
| GLU | E | GAA GAG |
| GLY | G | GGT GGC GGA GGG |
| HIS | H | CAT CAC |
| ILE | I | ATT ATC ATA |
| LEU | L | CTT CTC CTA CTG TTA TTG |
| LYS | K | AAA AAG |
| MET | M | ATG |
| PHE | F | TTT TTC |
| PRO | P | CCT CCC CCA CCG |
| SER | S | TCT TCC TCA TCG AGT AGC |
| THR | T | ACT ACC ACA ACG |
| TRP | H | TGG |
| TYR | Y | TAT TAC |

| | | |
|---|---|---|
| VAL | V | GTT GTC GTA GTG |
| *** | * | TAA TAG TGA |

What is claimed is:

1. A method for determining the effectiveness of an agent for inhibiting a Human Immunodeficiency Virus Type 2 (HIV-2) from binding to a target cell, said method comprising:

contacting said cell with said agent to be tested in the presence and in the absence of a labeled peptide having immunological properties of a first portion of the envelope glycoprotein of an HIV-2 virus, wherein said peptide comprises no more than about 40 amino acid residues, said first portion of the envelope glycoprotein is antigenic or is capable of eliciting the production of antibodies directed to the peptide, and said envelope glycoprotein comprises an amino acid sequence as follows:

MetMetAsnGlnLeuLeuIleAlaIleLeuLeuAlaSerAlaCys
10
LeuValTyrCysThrGlnTyrValThrValPheTyrGlyValPro
20           30
ThrTrpLysAsnAlaThrIleProLeuPheCysAlaThrArgAsn
40
ArgAspThrTrpGlyThrIleGlnCysLeuProAspAsnAspAsp
50           60
TryGlnGluIleThrLeuAsnValThrGluAlaPheAspAlaTrp
70
AsnAsnThrValThrGluGlnAlaIleGluAspValTrpHisLeu
80           90
PheGluThrSerIleLysProCysValLysLeuThrProLeuCys
100
ValAlaMetLysCysSerSerThrGluSerSerThrGlyAsnAsn
110           120
ThrThrSerLysSerThrSerThrThrThrThrThrProThrAsp
130
GlnGluGlnGluIleSerGluAspThrProCysAlaArgAlaAsp
140           150
AsnCysSerGlyLeuGlyGluGluGluThrIleAsnCysGlnPhe
160
AsnMetThrGlyLeuGluArgAspLysLysLysGlnTyrAsnGlu
170           180
ThrTrpTyrSerLysAspValValCysGluThrAsnAsnSerThr
190
AsnGlnThrGlnCysTyrMetAsnHisCysAsnThrSerValIle 200           210
ThrGluSerCysAspLysHisTyrTrpAspAlaIleArgPheArg
220
TyrCysAlaProProGlyTyrAlaLeuLeuArgCysAsnAspThr
230           240
AsnTyrSerGlyPheAlaProAsnCysSerLysValValAlaSer
250
ThrCysThrArgMetMetGluThrGlnThrSerThrTrpPheGly
260           270
PheAsnGlyThrArgAlaGluAsnArgThrTyrIleTyrTrpHis
280
GlyArgAspAsnArgThrIleIleSerLeuAsnLysTryTyrAsn
290           300
LeuSerLeuHisCysLysArgProGlyAsnLysThrValLysGln
310
IleMetLeuMetSerGlyHisValPheHisSerHisTyrGlnPro
320           340
IleAsnLysArgProArgGlnAlaTrpCysTrpPheLysGlyLys
350
TrpLysAspAlaMetGlnGluValLysThrLeuAlaLysHisPro
360           370
ArgTyrArgGlyThrAsnAspThrArgAsnIleSerPheAlaAla
380
ProGlyLysGlySerAspProGluValAlaTyrMetTrpThrAsn
390           400
CysArgGlyGluPheLeuTyrCysAsnMetThrTrpPheLeuAsn
410
TrpIleGluAsnLysThrHisArgAsnTyrAlaProCysHisIle
420           430
LysGlnIleIleAsnThrTrpHisLysValGlyArgAsnValTyr
440
LeuProProArgGluGlyGluLeuSerCysAsnSerThrValThr
450           460
SerIleIleAlaAsnIleAspTrpGlnAsnAsnAsnGlnThrAsn
470
IleThrPheSerAlaGluValAlaGluLeuTyrArgLeuGluLeu

-continued

```
              480                      490
GlyAspTyrLysLeuValGluIleThrProIleGlyPheAlaPro

500
ThrLysGluLysArgTyrSerSerAlaHisGlyArgHisThrArg 510                      520
GlyValPheValLeuGlyPheLeuGlyPheLeuAlaThrAlaGly

530
SerAlaMetGlyAlaArgAlaSerLeuThrValSerAlaGlnSer 540                      550
ArgThrLeuLeuAlaGlyIleValGlnGlnGlnGlnGlnLeuLeu

560
AspValValLysArgGlnGlnGluLeuLeuArgLeuThrValTrp 570                      580
GlyThrLysAsnLeuGlnAlaArgValThrAlaIleGluLysTyr

590
LeuGluAspGlnAlaArgLeuAsnSerTrpGlyCysAlaPheArg 600                      610
GlnValCysHisThrThrValProTrpValAsnAspSerLeuAla

620
ProAspTrpAspAsnMetThrTrpGlnGluTrpGluLysGlnVal 630                      640
ArgTyrLeuGluAlaAsnIleSerLysSerLeuGluGluAlaGln

650
IleGlnGlnGluLysAsnMetTyrGluLeuGlnLysLeuAsnSer 660                      670
TrpAspIlePheGlyAsnTrpPheAspLeuThrSerTrpValLys

680
TyrIleGlnTyrGlyValLeuIleIleValAlaValIleAlaLeu 690                      700
ArgIleValIleTyrValValGlnMetLeuSerArgLeuArgLys

710
GlyTyrArgProValPheSerSerProProGlyTyrIleGln***

720                      730
IleHisIleHisLysAspArgGlyGlnProAlaAsnGluGluThr

740
GluGluAspGlyGlySerAsnGlyGlyAspArgTyrTrpProTrp 750                      760
ProIleAlaTyrIleHisPheLeuIleArgGlnLeuIleArgLeu

770
LeuThrArgLeuTyrSerIleCysArgAspLeuLeuSerArgSer
```

-continued

```
              780                      790
PheLeuThrLeuGlnLeuIleTyrGlnAsnLeuArgAspTrpLeu

800
ArgLeuArgThrAlaPheLeuGlnTyrGlyCysGluTrpIleGln 810                      820
GluAlaPheGlnAlaAlaAlaArgAlaThrArgGluThrLeuAla

830
GlyAlaCysArgGlyLeuTrpArgValLeuGluArgIleGlyArg 840                      850
GlyIleLeuAlaValProArgArgIleArgGlnGlyAlaGluIle

850
AlaLeuLeu***GlyThrAlaValSerAlaGlyArgLeuTyrGlu 860                      870
TyrSerMetGluGlyProSerSerArgLysGlyGluLysPheVal

880
GlnAlaThrLysTyrGly;

890
``` determining the amount of labeled peptide bound in the presence of said agent;

determining the amount of labeled peptide bound in the absence of said agent; and determining the relative amount of labeled peptide-cell binding in the presence of said agent compared to the amount of labeled peptide-cell binding in the absence of said agent;

wherein an agent having a low affinity for binding to the cell is evidenced by little or no change between the binding values of the labeled peptide in the presence and in the absence of the agent, and an agent having a high affinity for binding to the cell is evidenced by a lower binding value in the presence of the agent in comparison to the binding value in the absence of the agent.

2. The method of claim 1, wherein said enveloped glycoprotein is labeled with an immunoassay label selected from the group consisting of enzymes, radioactive isotopes, fluorescent labels, and chromophores.

3. A method for determining the effectiveness of an agent for inhibiting a Human Immunodeficiency Virus Type 2 (HIV-2) from binding to a target cell, said method comprising:

contacting said cell with said agent to be tested in the presence of in the absence of one or more labeled peptides selected from the group consisting of:

(1) a peptide comprising an amino acid sequence of either of the following formulas:

XR--A-E-YL-DQ--L--WGC-----CZ, or

XA-E-YL-DZ, wherein X and Z are OH or $NH_2$, and wherein each of the hyphens corresponds to an aminoacyl residue selected from the group consisting of those which permit the conservation of the immunological properties of either of the following peptide sequences:
RVTAIEKYLQDQARLNSWGCAFRQVC, or
AIEKYLQDQ;

(2) a peptide comprising an amino acid sequence of either of the following formulas:
X----E--Q-QQEKN--EL--L---Z, or
XQ-QQEKNZ,
wherein X and Z are OH or NH$_2$, and wherein each of the hyphens corresponds to an aminoacyl residue selected from the group consisting of those which permit the conservation of the immunological properties of either of the following peptide sequences:
SKSLEQAQIQQEKNMYELQKLNSW, or
QIQQEKN;

(3) a peptide comprising an amino acid sequence of either of the following formulas:
XEL--YK-V-I-P-G-APTK-KR-----Z, or
XYK-V-I-P-G-APTK-KRZ,
wherein X and Z are OH or NH$_2$, and wherein each of the hyphens corresponds to an aminoacyl residue selected from the group consisting of those which permit the conservation of the immunological properties of either of the following peptide sequences:

ELGDYKLVEITPIGFAPTKEKRYSSAH, or

YKLVEITPIGFAPTKEK;

(4) the antigenic peptide gagl comprising an amino acid sequence of the following formula:

XNCKLVLKGLGMNPTLEEMLTAZ, wherein X and Z or OH or NH2, and wherein each of the hyphens corresponds to an aminoacyl residue selected from the group consisting of those which permit the conservation of the immunological properties of the following peptide sequence:

XNCKLVLKGLGMNPTLEEMLTA;

(5) a peptide comprising an amino acid sequence of either of the following formulas:

X----VTV-YGVP-WK-AT--LFCA-Z, or

XVTV-YGVP-WK-ATZ, wherein X and Z are OH or $NH_2$, and wherein each of the hyphens corresponds to an aminoacyl residue selected from the group consisting of those which permit the conservation of the immunological properties of either of the following peptide sequences:

CTQYVTVFYGVPTWKNATIPLFCAT, or VTVFYGVPTWKNAT;

(6) a peptide comprising an amino acid sequence of either of the following formulas:

X-G-DPE------NC-GEF-YCN-----NZ, or

XNC-GEF-YCNZ, wherein X and Z are OH or $NH_2$, and wherein each of the hyphens corresponds to an aminoacyl residue selected from the group consisting of those which permit the conservation of the immunological properties of either of the following peptide sequences:

KGSDPEVAYMWTNCRGEFLYCNMTWFLN, or

NCRGEFLYCN;

(7) a peptide comprising an amino acid sequence of either of the following formulas:

X-----C-IKQ-I------G---YZ, or

XC-IKQ-IZ, wherein X and Z are OH or $NH_2$, and wherein each of the hyphens corresponds to an aminoacyl residue selected from the group consisting of those which permit the conservation of the immunological properties of either of the following peptide sequences:

RNYAPCHIKQIINTWHKVGRNVY, or

CHIKQII;

(8) a peptide comprising an amino acid sequence of either of the following formulas:

X---QE--LNVTE-F--W-NZ, or

XLNVTE-FZ, wherein X and Z are OH or $NH_2$, and wherein each of the hyphens corresponds to an aminoacyl residue selected from the group consisting of those which permit the conservation of the immunological properties of the following peptide sequence:

DDYQEITLNVTEAFDAWNN;

(9) a peptide comprising an amino acid sequence of either of the following formulas:

XL---S-KPCVKLTPLCV--KZ, or

XKPCVKLTPLCVZ, or

XS-KPCVKLTPLCVZ, wherein X and Z are OH or $NH_2$, and wherein each of the hyphens corresponds to an aminoacyl residue selected from the group consisting of those which permit the conservation of the immunological properties of the following peptide sequence:

ETSIKPCVKLTPLCVAMK;

(10) a peptide comprising an amino acid sequence of either of the following formulas:

X---N-S-IT--C-Z, or

XN-S-ITZ, wherein X and Z are OH or $NH_2$, and wherein each of the hyphens corresponds to an aminoacyl residue selected from the group consisting of those which permit the conservation of the immunological properties of the following peptide sequence:

NHCNTSVITESCD;

(11) a peptide comprising an amino acid sequence having the following formula:

XYC-P-G-A-L-CN-TZ, wherein X and Z are OH or $NH_2$, and wherein each of the hyphens corresponds to an aminoacyl residue selected from the group consisting of those which permit the conservation of the immunological properties of the following peptide sequence:

YCAPPGYALLRCNDT; and

(12) a peptide comprising an amino acid sequence of either of the following formulas:

X------A-C-----W--Z, wherein X and Z are OH or $NH_2$, and wherein each of the hyphens corresponds to an aminoacyl residue selected from the group consisting of those which permit the conservation of the immunological properties of the following peptide sequence:

NKRPRQAWCWFKGKWKD;

wherein said immunological properties comprise the ability of said peptide sequences to specifically recognize antibodies against HIV-2;

determining the amount of labeled peptide bound in the presence of said agent;

determining the amount of labeled peptide bound in the absence of said agent; and determining the relative amount of labeled peptide-cell binding in the presence of said agent compared to the amount of labeled peptide-cell binding in the absence of said agent;

wherein an agent having a low affinity for binding to the cell is evidenced by little or no change between the binding values of the labeled peptide in the presence and in the absence of the agent, and an agent having a high affinity for binding to the cell is evidenced by a lower binding value in the presence of the agent in comparison to the binding value in the agent in comparison to the binding value in the absence of the agent.

4. The method of claim 3, wherein said one or more peptides are labeled with an immunoassay label selected from the group consisting of enzymes, radioactive isotopes, fluorescent labels, and chromophores.

5. A kit for determining the effectiveness of an agent for inhibiting a Human Immunodeficiency Virus Type 2 (HIV-2) from binding to a target cell, said kit comprising:

a labeled peptide having immunological properties of a first portion of the envelope glycoprotein of a HIV-2 virus, wherein said peptide comprises no more than about 40 amino acid residues, said first portion of the envelope glycoprotein is antigenic or is capable of eliciting the production of antibodies directed to the peptide, and said envelope glycoprotein comprises an amino acid sequence as follows:

```
MetMetAsnGlnLeuLeuIleAlaAlaIleLeuLeuAlaSerAlaCys
                                              10

LeuValTyrCysThrGlnTyrValThrValPheTyrGlyValPro
                20                            30

ThrTrpLysAsnAlaThrIleProLeuPheCysAlaThrArgAsn
                                              40

ArgAspThrTrpGlyThrIleGlnCysLeuProAspAsnAspAsp
                50                            60

TryGlnGluIleThrLeuAsnValThrGluAlaPheAspAlaTrp
                                              70

AsnAsnThrValThrGluGlnAlaIleGluAspValTrpHisLeu
                80                            90

PheGluThrSerIleLysProCysValLysLeuThrProLeuCys
                                             100

ValAlaMetLysCysSerSerThrGluSerSerThrGlyAsnAsn
               110                           120

ThrThrSerLysSerThrSerThrThrThrThrThrProThrAsp
                                             130

GlnGluGlnGluIleSerGluAspThrProCysAlaArgAlaAsp
               140                           150

AsnCysSerGlyLeuGlyGluGluGluThrIleAsnCysGlnPhe
                                             160

AsnMetThrGlyLeuGluArgAspLysLysLysGlnTyrAsnGlu
               170                           180

ThrTrpTyrSerLysAspValValCysGluThrAsnAsnSerThr
                                             190

AsnGlnThrGlnCysTyrMetAsnHisCysAsnThrSerValIle
               200                           210

ThrGluSerCysAspLysHisTyrTrpAspAlaIleArgPheArg
                                             220

TyrCysAlaProProGlyTyrAlaLeuLeuArgCysAsnAspThr
               230                           240

AsnTyrSerGlyPheAlaProAsnCysSerLysValValAlaSer
                                             250

ThrCysThrArgMetMetGluThrGlnThrSerThrTrpPheGly
               260                           270
```

-continued
```
PheAsnGlyThrArgAlaGluAsnArgThrTyrIleTyrTrpHis
                                             280

GlyArgAspAsnArgThrIleIleSerLeuAsnLysTryTyrAsn
               290                           300

LeuSerLeuHisCysLysArgProGlyAsnLysThrValLysGln
                                             310

IleMetLeuMetSerGlyHisValPheHisSerHisTyrGlnPro
               320                           340

IleAsnLysArgProArgGlnAlaTrpCysTrpPheLysGlyLys
                                             350

TrpLysAspAlaMetGlnGluValLysThrLeuAlaLysHisPro
               360                           370

ArgTyrArgGlyThrAsnAspThrArgAsnIleSerPheAlaAla
                                             380

ProGlyLysGlySerAspProGluValAlaTyrMetTrpThrAsn
               390                           400

CysArgGlyGluPheLeuTyrCysAsnMetThrTrpPheLeuAsn
                                             410

TrpIleGluAsnLysThrHisArgAsnTyrAlaProCysHisIle
               420                           430

LysGlnIleIleAsnThrTrpHisLysValGlyArgAsnValTyr
                                             440

LeuProProArgGluGlyGluLeuSerCysAsnSerThrValThr
               450                           460

SerIleIleAlaAsnIleAspTrpGlnAsnAsnAsnGlnThrAsn
                                             470

IleThrPheSerAlaGluValAlaGluLeuTyrArgLeuGluLeu
               480                           490

GlyAspTyrLysLeuValGluIleThrProIleGlyPheAlaPro
                                             500

ThrLysGluLysArgTyrSerSerAlaHisGlyArgHisThrArg
               510                           520

GlyValPheValLeuGlyPheLeuGlyPheLeuAlaThrAlaGly
                                             530

SerAlaMetGlyAlaArgAlaSerLeuThrValSerAlaGlnSer
               540                           550

ArgThrLeuLeuAlaGlyIleValGlnGlnGlnGlnGlnLeuLeu
                                             560

AspValValLysArgGlnGlnGluLeuLeuArgLeuThrValTrp
               570                           580

GlyThrLysAsnLeuGlnAlaArgValThrAlaIleGluLysTyr
                                             590

LeuGluAspGlnAlaArgLeuAsnSerTrpGlyCysAlaPheArg
               600                           610

GlnValCysHisThrThrValProTrpValAsnAspSerLeuAla
                                             620

ProAspTrpAspAsnMetThrTrpGlnGluTrpGluLysGlnVal
               630                           640

ArgTyrLeuGluAlaAsnIleSerLysSerLeuGluGluAlaGln
                                             650

IleGlnGlnGluLysAsnMetTyrGluLeuGlnLysLeuAsnSer
               660                           670

TrpAspIlePheGlyAsnTrpPheAspLeuThrSerTrpValLys
                                             680
```

-continued

```
TyrIleGlnTyrGlyValLeuIleIleValAlaValIleAlaLeu
690                                         700

ArgIleValIleTyrValValGlnMetLeuSerArgLeuArgLys
                     710

GlyTyrArgProValPheSerSerProProGlyTyrIleGln***
720                                         730

IleHisIleHisLysAspArgGlyGlnProAlaAsnGluGluThr
                     740

GluGluAspGlyGlySerAsnGlyGlyAspArgTyrTrpProTrp
750                                         760

ProIleAlaTyrIleHisPheLeuIleArgGlnLeuIleArgLeu
                     770

LeuThrArgLeuTyrSerIleCysArgAspLeuLeuSerArgSer
780                                         790

PheLeuThrLeuGlnLeuIleTyrGlnAsnLeuArgAspTrpLeu
                     800

ArgLeuArgThrAlaPheLeuGlnTyrGlyCysGluTrpIleGln
810                                         820

GluAlaPheGlnAlaAlaAlaArgAlaThrArgGluThrLeuAla
                     830

GlyAlaCysArgGlyLeuTrpArgValLeuGluArgIleGlyArg
840                                         850

GlyIleLeuAlaValProArgArgIleArgGlnGlyAlaGluIle
                     850

AlaLeuLeu***GlyThrAlaValSerAlaGlyArgLeuTyrGlu
860                                         870

TyrSerMetGluGlyProSerSerArgLysGlyGluLysPheVal
                     880

GlnAlaThrLysTyrGly;
        890
``` a composition comprising a target cell; and a control composition comprising said labeled peptide and said cell;

wherein the relative affinity of the agent for binding to the cell is determined by comparing the amount of labeled peptide bound in the presence of the agent with the amount of labeled peptide bound in the absence of said agent.

6. The kit of claim 5, wherein said enveloper glycoprotein is labeled with an immunoassay label selected from the group consisting of enzymes, radioactive isotopes, fluorescent labels, and chromophores.

7. A kit for determining the effectiveness of an agent for inhibiting a Human Immunodeficiency Virus Type 2 (HIV-2) from binding to a target cell, said kit comprising:

one or more labeled peptides selected from the group consisting of:

(1) a peptide comprising an amino acid sequence of either of the following formulas:

XR--A-E-YL-DQ--L--WGC-----CZ, or

XA-E-YL-DZ, wherein X and Z are OH or $NH_2$, and wherein each of the hyphens corresponds to an aminoacyl residue selected from the group consisting of those which permit the conservation of the immunological properties of either of the following peptide sequences:

RVTAIEKYLQDQARLNSWGCAFRQVC, or

AIEKYLQDQ;

(2) a peptide comprising an amino acid sequence of either of the following formulas:

X ----E--Q-QQEKN--EL--L---Z, or

XQ-QQEKNZ, wherein X and Z are OH or $NH_2$, and wherein each of the hyphens corresponds to an aminoacyl residue selected from the group consisting of those which permit the conservation of the immunological properties of either of the following peptide sequences:

SKSLEQAQIQQEKNMYELQKLNSW, or

QIQQEKN;

(3) a peptide comprising an amino acid sequence of either of the following formulas:

XEL--YK-V-I-P-G-APTK-KR-----Z, or

XYK-V-I-P-G-APTK-KRZ, wherein X and Z are OH or $NH_2$, and wherein each of the hyphens corresponds to an aminoacyl residue selected from the group consisting of those which permit the conservation of the immunological properties of either of the following peptide sequences:

ELGDYKLVEITPIGFAPTKEKRYSSAH, or

YKLVEITPIGFAPTKEK;

(4) the antigenic peptide gagl comprising an amino acid sequence of the following formula:

XNCKLVLKGLGMNPTLEEMLTAZ, wherein X and Z are OH or $NH_2$, and wherein each of the hyphens corresponds to an aminoacyl residue selected from the group consisting of those which permit the conservation of the immunological properties of the following peptide sequence:

XNCKLVLKGLGMNPTLEEMLTA;

(5) a peptide comprising an amino acid sequence of either of the following formulas:

X----VTV-YGVP-WK-AT--LFCA-Z, or

XVTV-YGVP-WK-ATZ, wherein X and Z are OH or $NH_2$, and wherein each of the hyphens corresponds to an aminoacyl residue selected from the group consisting of those which permit the conservation of the immunological properties of either of the following peptide sequences:

CTQYVTVFYGVPTWKNATIPLFCAT, or

VTVFYGVPTWKNAT;

(6) a peptide comprising an amino acid sequence of either of the following formulas:

X-G-DPE------NC-GEF-YCN-----NZ, or

XNC-GEF-YCNZ, wherein X and Z are OH or $NH_2$, and wherein each of the hyphens corresponds to an aminoacyl residue selected from the group consisting of those which permit the conservation of the immunological properties of either of the following peptide sequences:

KGSDPEVAYMWTNCRGEFLYCNMTWFLN, or

NCRGEFLYCN;

(7) a peptide comprising an amino acid sequence of either of the following formulas:

X-----C-IKQ-I------G---YZ, or

XC-IKQ-IZ, wherein X and Z are OH or $NH_2$, and wherein each of the hyphens corresponds to an aminoacyl residue selected from the group consisting of those which permit the conservation of the immunological properties of either of the following peptide sequences:

RNYAPCHIKQIINTWHKVGRNVY, or

CHIKQII;

(8) a peptide comprising an amino acid sequence of either of the following formulas:

X---QE--LNVTE-F--W-NZ, or

XLNVTE-FZ, wherein X and Z are OH or $NH_2$, and wherein each of the hyphens corresponds to an aminoacyl residue selected from the group consisting of those which permit the conservation of the immunological properties of the following peptide sequence:

DDYQEITLNVTEAFD

UNITED STATES PATENT AND TRADEMARK OFFICE
CERTIFICATE OF CORRECTION

PATENT NO.: 5,976,785

DATED: November 2, 1999

INVENTOR(S): Marc ALIZON et al.

It is certified that an error appears in the above-identified patent and that said Letters Patent is hereby corrected as shown below:

In the Claims:
Claim 1, col. 35, line 37 and col. 36, line 27, "Try" should read --Tyr--.

Claim 3, col. 38, line 57, "presence of" should read --presence or--;
    col. 39, line 31, "NH2" should read --$NH_2$--.

Claim 5, col. 41, line 34, and col. 42, line 5, "Try" should read --Tyr--.

Claim 6, col. 43, line 46, "enveloper" should read --envelope--.

Claim 8, col. 45, line 56, "peptide" should read --peptides--.

Signed and Sealed this

Twenty-third Day of May, 2000

Attest:

Q. TODD DICKINSON

*Attesting Officer*   *Director of Patents and Trademarks*